United States Patent [19]
Holton et al.

[11] Patent Number: 5,250,683
[45] Date of Patent: Oct. 5, 1993

[54] CERTAIN SUBSTITUTED TAXANES AND PHARMACEUTICAL COMPOSITIONS CONTAINING THEM

[75] Inventors: Robert A. Holton; Hossain Nadizadeh; Seokchan Kim; Ronald J. Beidiger, all of Tallahassee, Fla.

[73] Assignee: Florida State University, Tallahassee, Fla.

[21] Appl. No.: 863,451

[22] Filed: Apr. 3, 1992

Related U.S. Application Data

[63] Continuation-in-part of Ser. No. 763,805, Sep. 23, 1991, abandoned.

[51] Int. Cl.$^5$ .................. C07D 417/08; C07D 305/14
[52] U.S. Cl. ......................... 544/60; 544/147; 544/162; 544/379; 546/196; 546/212; 546/214; 548/525; 548/527; 549/435; 549/448; 549/473; 549/510; 549/511

[58] Field of Search ................. 544/60, 147, 162, 379; 546/196, 212, 214; 548/525, 527; 549/435, 448, 473, 510, 511

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,924,011 | 5/1990 | Denis et al. | 849/510 |
| 4,924,012 | 5/1990 | Colin et al. | 849/510 |
| 4,942,184 | 7/1990 | Haugwitz et al. | 514/449 |
| 5,015,744 | 5/1991 | Holton | 549/510 |
| 5,059,699 | 10/1991 | Kingston et al. | 549/511 |

FOREIGN PATENT DOCUMENTS

| | | |
|---|---|---|
| 253738 | 7/1987 | European Pat. Off. . |
| 253739 | 7/1987 | European Pat. Off. . |
| 336840 | 4/1989 | European Pat. Off. . |
| 336841 | 4/1989 | European Pat. Off. . |
| 9010443 | 9/1990 | PCT Int'l Appl. . |
| 9209589 | 6/1992 | PCT Int'l Appl. . |
| 919224 | 11/1991 | South Africa . |

OTHER PUBLICATIONS

H. M. Deutsch et al., "Synthesis of Congeners and Prodrugs. 3. Water-Soluble Prodrugs of Taxol with Potent Antitumour Activity", Jour. of Med. Chem., vol. 32, No. 4, pp. 788-792 (Apr. 1989).

N. F. Magri et al., "Modified Taxols, 4. Synthesis & Biological Activity of Taxols Modified in the Side Chain", vol. 51, No. 2, pp. 298-306 (1988).

Denis and Greene, "A Highly Efficient, Practical Approach to Natural Taxol", J. Am. Chem. Soc. 1988, 110, 5917-5919.

Holton et al., "A Synthesis of Taxusin", J. Am. Chem. Soc., 1988, 110, pp. 6558-6560.

Holton, "Synthesis of the Taxane Ring System", J. Am. Chem. Soc., 1984, 106, pp. 5731-5732.

Mukerjee et al., "β-Lactams: Retrospect and Prospect", Tetrahedron vol. 34, Report No. 52, pp. 1731-1767 (1978).

Wani et al., "Plant Antitumor Agents. VI. The Isolation and Structure of Taxol, a Novel Antileukemic and Antitumor Agent from Taxus Brevifolia", J. Am. Chem. Soc. 93:9, May 5, 1971, pp. 2325-2327.

Primary Examiner—Alan L. Rotman
Assistant Examiner—Ba K. Trinh
Attorney, Agent, or Firm—Senniger, Powers, Leavitt & Roedel

[57] ABSTRACT

A taxane derivative of the formula

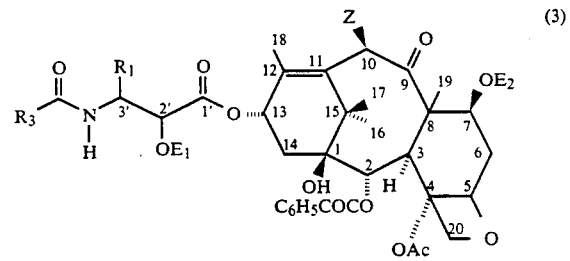

(3)

wherein
R$_1$ and R$_3$ are independently selected from the group comprising phenyl, naphthalene, C$_6$H$_5$CHCH—, and
(Abstract continued on next page.)

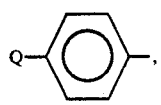

provided, however,
$R_1$ and $R_3$ are not both phenyl;
Q is $CH_3-$, $(CH_3)_3C-$, $CH_3O-$, Cl, Br, F, $NO_2$,

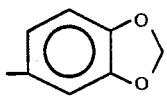

or

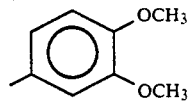

Z is $-OT_1$,
$T_1$ is hydrogen, hydroxyl protecting group, or $-COT_2$,
$T_2$ is H, $C_1-C_6$ alkyl, $C_1-C_6$ alkenyl, $C_1-C_6$ alkynyl or monocylic aryl,
Ac is acetyl, and
$E_1$ and $E_2$ are independently selected from hydrogen and functional groups which increase the water solubility of the taxane derivative are useful as antitumor agents.

20 Claims, No Drawings

CERTAIN SUBSTITUTED TAXANES AND PHARMACEUTICAL COMPOSITIONS CONTAINING THEM

REFERENCE TO RELATED APPLICATIONS

This application is a continuation-in-part application of U.S. Ser. No. 07/763,805, filed Sep. 23, 1991 now abandoned.

BACKGROUND OF THE INVENTION

The present invention is directed to novel taxanes which have utility as antileukemia and antitumor agents.

The taxane family of terpenes, of which taxol is a member, has attracted considerable interest in both the biological and chemical arts. Taxol is a promising cancer chemotherapeutic agent with a broad spectrum of antileukemic and tumor-inhibiting activity. Taxol has a 2'R, 3'S configuration and the following structural formula:

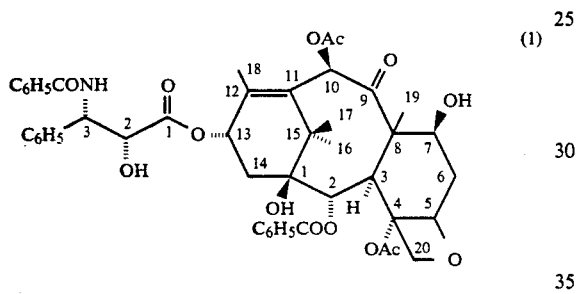

wherein Ac is acetyl. Because of this promising activity, taxol is currently undergoing clinical trials in both France and the United States.

Colin et al. reported in U.S. Pat. No. 4,814,470 that taxol derivatives having structural formula (2) below, have an activity significantly greater than that of taxol (1).

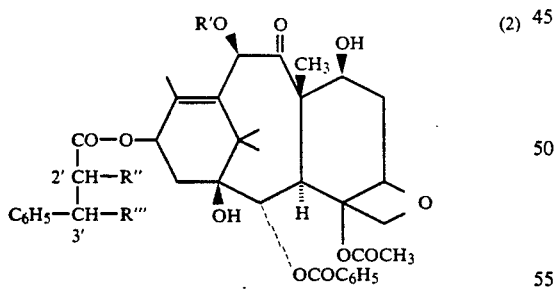

R' represents hydrogen or acetyl and one of R" and R'" represents hydroxy and the other represents tert-butoxy-carbonylamino and their stereoisomeric forms, and mixtures thereof. The compound of formula (2) in which R" is hydroxy, R'" is tert-butoxycarbonylamino having the 2'R, 3'S configuration is commonly referred to as taxotere.

Although taxol and taxotere are promising chemotherapeutic agents, they are not universally effective. Accordingly, a need remains for additional chemotherapeutic agents.

SUMMARY OF THE INVENTION

Among the objects of the present invention, therefore, is the provision of novel taxane derivatives which are valuable antileukemia and antitumor agents.

Briefly, therefore, the present invention is directed to taxane derivatives of the formula:

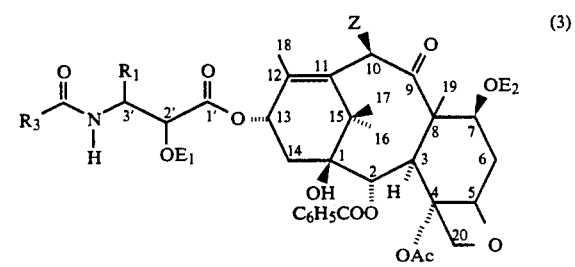

wherein $R_1$ and $R_3$ are independently selected from the group comprising phenyl, naphthyl, $C_6H_5CHCH-$, and

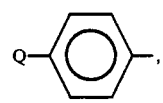

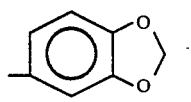

or

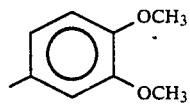

provided, however, $R_1$ and $R_3$ are not both phenyl;

Q is $CH_3-$, $(CH_3)_3C-$, $CH_3O-$, Cl, Br, F, $-NO_2$,

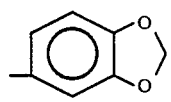

or

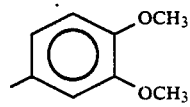

Z is $-OT_1$, $T_1$ is hydrogen, hydroxyl protecting group, or $-COT_2$, $T_2$ is H, $C_1-C_6$ alkyl, $C_2-C_6$ alkenyl, $C_2-C_6$ alkynyl or monocylic aryl, Ac is acetyl, and $E_1$ and $E_2$ are independently selected from hydrogen, hydroxy protecting groups and functional groups which increase the water solubility of the taxane derivative.

Other objects and features of this invention will be in part apparent and in part pointed out hereinafter.

DETAILED DESCRIPTION OF THE PREFERRED EMBODIMENTS

In accordance with the present invention, it has been discovered that compounds having structural formula (3) show remarkable properties, in vitro, and are valuable antileukemia and antitumor agents. Their biological activity has been determined in vitro, using tubulin assays according to the method of Parness et al., J. Cell Biology, 91:479–487 (1981) and human cancer cell lines, and is comparable to that exhibited by taxol and taxotere.

Taxane derivatives having formula (3) may be obtained by reacting a β-lactam with metal alkoxides having the taxane tetracyclic nucleus and a C-13 metallic oxide substituent to form compounds having a β-amido ester substituent at C-13. The β-lactams have the following structural formula:

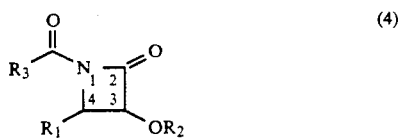

wherein
$R_1$ and $R_3$ are as previously defined, and $R_2$ is a hydroxy protecting group, β-lactams (4) can be prepared from readily available starting materials, as is illustrated by the following reaction scheme:

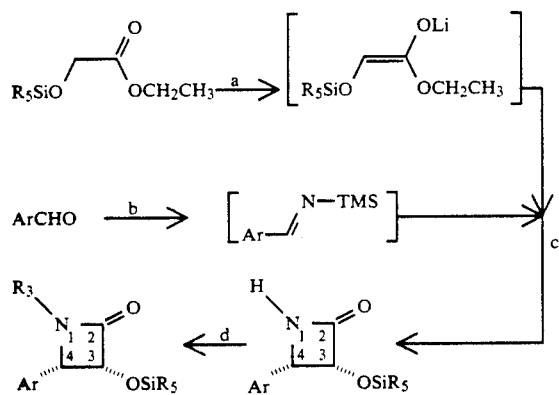

reagents
(a) LDA, THF, −78° C. to −50° C.;
(b) LHMDS, THF, −78° C. to 0° C.;
(c) THF, −78° C. to 25° C., (2h); and
(d) triethylamine and an acyl chloride

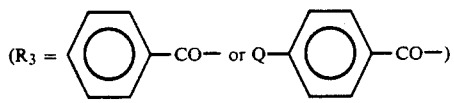

The 3-hydroxyl protecting group shown in the above reaction scheme is —SiR$_5$ wherein R$_5$ is trialkyl or triaryl such as triethyl. The 3-hydroxyl may be protected with other standard protecting groups such as 1-ethoxyethyl, or 2,2,2-trichloroethoxymethyl. Additional hydroxy protecting groups and the synthesis thereof may be found in "Protective groups in Organic Synthesis" by T. W. Greene, John Wiley & Sons, 1981.

The racemic β-lactams may be resolved into the pure enantiomers prior to protection by recrystallization of the corresponding 2-methoxy-2-(trifluoromethyl) phenylacetic esters. However, the reaction described hereinbelow in which the β-amido ester side chain is attached has the advantage of being highly diastereo-selective, thus permitting the use of a racemic mixture of side chain precursor.

The metal alkoxides having the taxane tetracyclic nucleus and a C-13 metallic oxide substituent have the following structural formula:

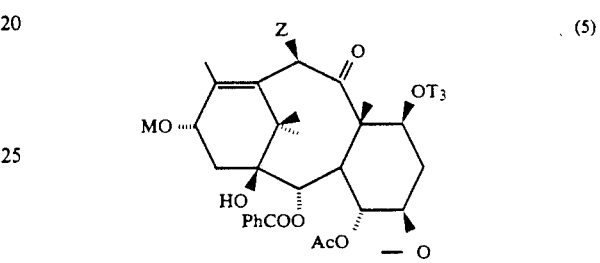

wherein Z is —OT$_1$; T$_1$ is hydrogen, hydroxyl protecting group, or —COT$_2$; T$_2$ is H, C$_1$–C$_6$ alkyl, C$_1$–C$_6$ alkenyl, C$_1$–C$_2$ alkynyl or monocylic aryl; T$_3$ is a hydroxy protecting group; and M is a metal, preferably selected from the group comprising Group IA, Group IIA and transition metals, and most preferably, Li, Mg, Na, K or Ti.

The metal alkoxides are prepared by reacting an alcohol having the taxane tetracyclic nucleus and a C-13 hydroxyl group with an organometallic compound in a suitable solvent. Preferably, the alcohol is a protected baccatin III, in particular, 7-O-triethylsilyl baccatin III (which can be obtained as described by Greene, et al. in JACS 110: 5917 (1988) or by other routes) or 7,10-bis-O-triethylsilyl baccatin III.

As reported in Greene et al., 10-deacetyl baccatin III is converted to 7-O-triethylsilyl-10-deacetyl baccatin III according to the following reaction scheme:

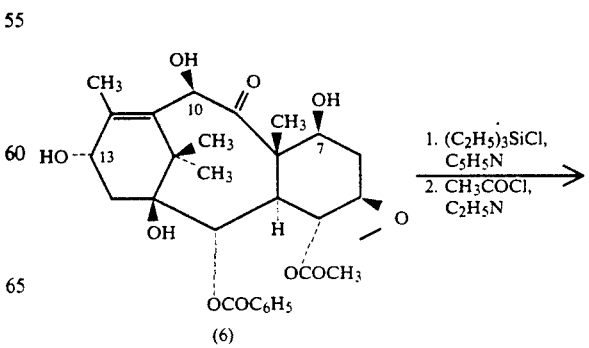

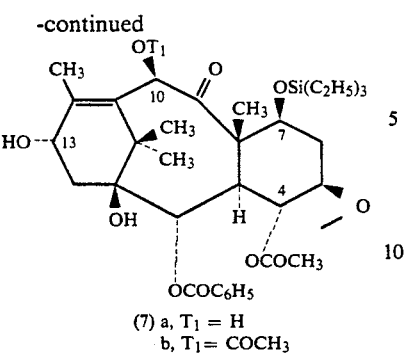

(7) a, T₁ = H
b, T₁ = COCH₃

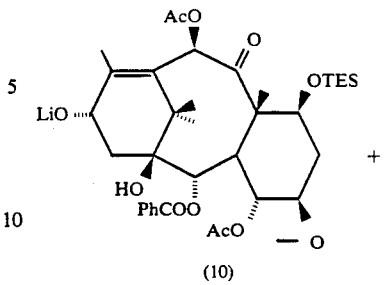

(10)

Under what is reported to be carefully optimized conditions, 10-deacetyl baccatin III is reacted with 20 equivalents of (C₂H₅)₃SiCl at 23° C. under an argon atmosphere for 20 hours in the presence of 50 ml of pyridine/mmol of 10-deacetyl baccatin III to provide 7-triethylsilyl-10-deacetyl baccatin III (7a) as a reaction product in 84–86% yield after purification. The reaction product may then optionally be acetylated with 5 equivalents of CH₃COCl and 25 mL of pyridine/mmol of 7a at 0° C. under an argon atmosphere for 48 hours to provide 86% yield of 7-O-triethylsilyl baccatin III (7b). Greene, et al. in JACS 110, 5917 at 5918 (1988).

The 7-O-triethylsilyl baccatin III (7b) is reacted with an organometallic compound such as n-butyllithium in a solvent such as tetrahydrofuran (THF), to form the metal alkoxide 13-O-lithium-7-O-triethylsilyl baccatin III (8) as shown in the following reaction scheme:

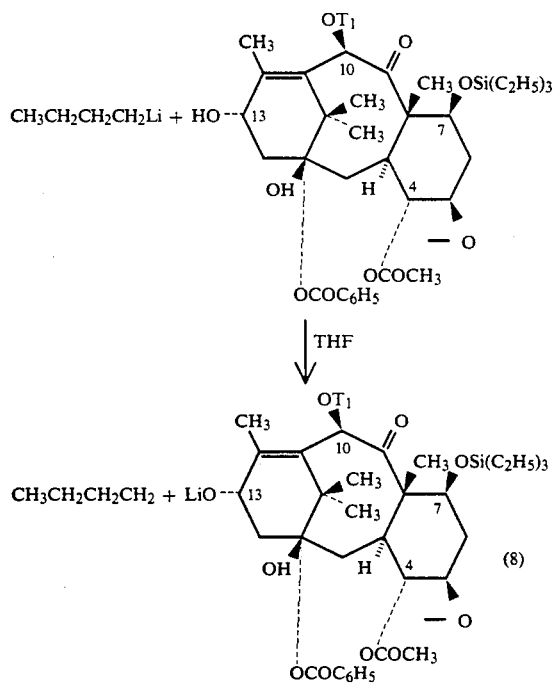

As shown in the following reaction scheme, 13-O-lithium-7-O-triethylsilyl baccatin III (8) reacts with β-lactam (4) in which R₂ is triethylsilyl to provide an intermediate in which the C-7 and C-2' hydroxyl groups are protected with a triethylsilyl group. The triethylsilyl groups are then hydrolyzed under mild conditions so as not to disturb the ester linkage or the taxane substituents.

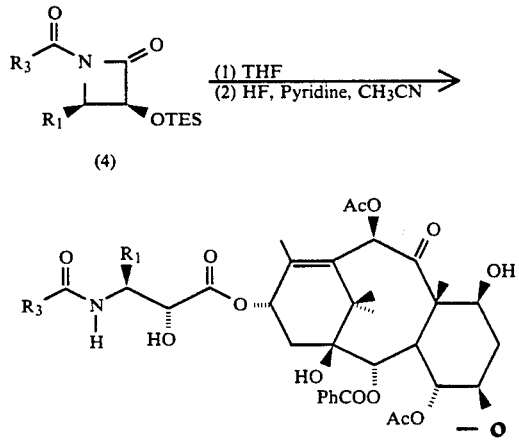

wherein
R₁ and R₃ are as previously defined,
Ac is acetyl, TES is triethylsilyl and Ph is phenyl.

Both the conversion of the alcohol to the metal alkoxide and the ultimate synthesis of the taxane derivative can take place in the same reaction vessel. Preferably, the β-lactam is added to the reaction vessel after formation therein of the metal alkoxide.

The present invention also provides pharmaceutical compositions containing a compound of formula (3) in combination with one or more pharmaceutically acceptable, inert or physiologically active, diluents or adjuvants.

These compositions may be presented in any form appropriate for the administration route envisaged. The parental route, and especially the intravenous route, is the preferential route for administration.

The compositions according to the invention for parenteral administration may be aqueous or nonaqueous sterile solutions, suspensions or emulsions. Propylene glycol, vegetable oils, especially olive oil, and injectable organic esters, e.g. ethyl oleate, may be used as the solvent or the vehicle. These compositions may also contain adjuvants, especially wetting agents, emulsifiers or dispersants. The sterilization may be carried out in several ways, e.g. using a bacteriological filter, by incorporating sterilizing agents into the composition, by irradiation or by heating. They may also be in the form of sterile solid compositions which may be dissolved or dispersed in sterile water or any other injectable sterile medium.

The products of general formula (3) are more particularly used in the treatment of acute leukemias and solid tumors, at daily doses which are generally between 1 and 2 mg/kg by the intravenous (perfusion) route for an adult.

The water solubility of compounds of formula (3) may be improved by modification of the C2' and/or C7 substituents to incorporate appropriate functional groups, $E_1$ and $E_2$. For increased water solubility, $E_1$ and $E_2$ may independently be hydrogen and —COG-COR$^1$ wherein G is ethylene, propylene, CH=CH, 1,2-cyclohexane, or 1,2-phenylene, $R^1$ = OH base, $NR^2R^3$, $OR^3$, $SR^3$, $OCH_2CONR^4R^5$, OH $R^2$ = hydrogen, methyl $R^3 = (CH_2)_nNR^6R^7$; $(CH)_nN^{\oplus}R^6R^7R^8X^{\ominus}$ n = 1 to 3

$R^4$ = hydrogen, lower alkyl containing 1 to 4 carbons $R^5$ = hydrogen, lower alkyl containing 1 to 4 carbons, benzyl, hydroxyethyl, $CH_2CO_2H$, dimethylaminoethyl $R^6R^7$ = lower alkyl containing 1 or 2 carbons, benzyl or $R^6$ and $R^7$ together with the nitrogen atom of $NR^6R^7$ form the following rings

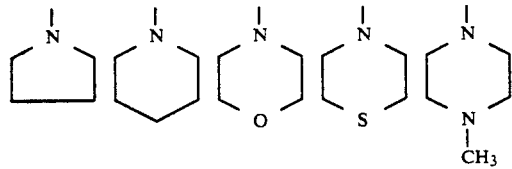

$R^8$ = lower alkyl containing 1 or 2 carbons, benzyl $X^{\ominus}$ = halide base = $NH_3$, $(HOC_2H_4)_3N$, $N(CH_3)_3$, $CH_3N(C_2H_4OH)_2$, $NH_2(CH_2)_6NH_2$, N-methylglucamine, NaOH, KOH.

The preparation of compounds in which $X_1$ or $X_2$ is —COGCOR$^1$ is set forth in Hangwitz U.S. Pat. No. 4,942,184 which is incorporated herein by reference.

The following examples illustrate the invention.

EXAMPLE 1

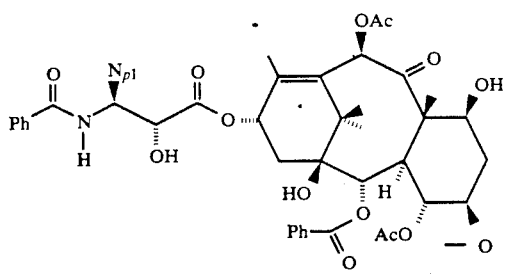

wherein $N_{pl}$ is

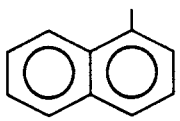

Preparation of 3'-desphenyl-3'-(1-naphthyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(1-naphthyl)azetidin-2-one (620 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 325 mg of a mixture containing (2'R,3'S)-2',7-(bis)triethylsilyl-3'-desphenyl-3'-(1-naphthyl) taxol and a small amount of the (2'S,3'R) isomer.

To a solution of 325 mg (0.287 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 260 mg of material which was purified by flash chromatography to give 166 mg (64%) of 3'-(1-naphthyl) taxol, which was recrystallized from methanol/water.

m.p. 164°-165° C.; $[\alpha]^{25}_{NA}$ −52.6° (c 0.005, CHCl$_3$).

$^1$H NMR (CDCl$_3$, 300 MHz) δ8.11 (d, J=7.1 Hz, 2H, benzoate ortho), 8.11 (m, 3H, aromatic), 7.91 (m, 3H, aromatic), 7.70 (m, 2H, aromatic), 7.63-7.46 (m, 7H, aromatic), 6.75 (d, J=8.8 Hz, 1H, NH), 6.52 (dd, J=8.8, 1.6 Hz, 1H, H3'), 6.27 (s, 1H, H10), 6.27 (dd, J=9.1, 9.1 Hz, 1H, H13), 5.68 (d, J=7.1 Hz, 1H, H2β), 4.85 (dd, J=7.6, 2.2 Hz, 1H, H5), 4.97 (dd, J=1.6 Hz, 1H, H2'), 4.39 (m, 1H, H7), 4.24 (d, J=8.5 Hz, 1H, H20α), 4.17 (d, J=8.5 Hz, 1H, H20β), 3.80 (d, J=7.1 Hz, 1H, H3), 3.65 (br, 1H, 2'OH), 2.55 (m, 1H, H6α), 2.48 (br, 1H, 7OH), 2.41 (s, 3H, 4Ac), 2.38 (m, 1H, H14), 1.96 (s, 3H, 10Ac), 1.86 (m, 1H, H6β), 1.80 (br s, 3H, Me18), 1.76 (s, 1H, 10H), 1.69 (s, 3H, Me19), 1.28 (s, 3H, Me17), 1.16 (s, 3H, Me16).

EXAMPLE 2

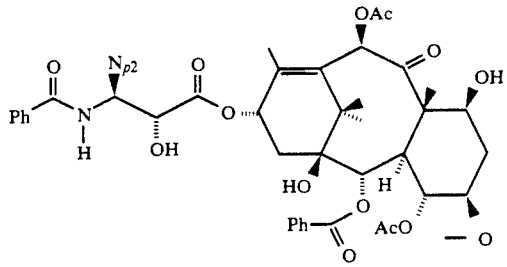

wherein $N_{p2}$ is

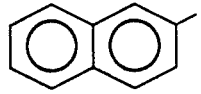

Preparation of 3'-desphenyl-3'-(2-naphthyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(2-naphthyl)azetidin-2-one (620 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residuo which was purified by filtration through silica gel to give 320 mg of a mixture containing (2'R,3'S)-2',7-(bis)triethylsilyl-3'-desphenyl-3'-(2-naphthyl) taxol and a small amount of the (2'S,3'R) isomer.

To a solution of 320 mg (0.283 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 255 mg of material which was purified by flash chromatography to give 166 mg (64%) of 3'-desphenyl-3'-(2-naphthyl) taxol, which was recrystallized from methanol/water.

m.p 164°-165° C.; $[\alpha]^{25}_{Na}$ −52.6° (c 0.005, CHCl$_3$).

$^1$H NMR (CDCl$_3$, 300 MHz) $\delta$8.14 (d, J=7.3 Hz, benzoate ortho), 7.96 (m, 1H, aromatic), 7.90 (m, 1H, aromatic), 7.85 (m, 2H, aromatic), 7.76 (m, 2H, aromatic), 7.60 (m, 3H, aromatic), 7.52 (m, 4H, aromatic), 7.41 (m, 2H, aromatic), 7.01 (d, J=8.8 Hz, 1H, NH), 6.27 (s, 1H, H10), 6.26 (dd, J=9.2, 9.2 Hz, 1H, H13), 5.97 (dd, J=8.8, 2.5 Hz, 1H, H3'), 5.68 (d, J=7.1 Hz, 1H, H2$\delta$), 4.93 (m, 1H, H5), 4.92 (m, 1H, H2'), 4.39 (m, 1H, H7), 4.30 (d, J=8.5 Hz, 1H, H20$\alpha$), 4.20 (d, J=8,5 Hz, 1H, H20$\beta$), 3.81 (d, J=7.1 Hz, 1H, H3), 3.60 (d, J=5 Hz, 1H, 2'OH), 2.48 (m, 1H, H6$\alpha$), 2.45 (br, 1H, 7OH), 2.39 (s, 3H, 4Ac), 2.30 (m, 2H, H14), 2.24 (s, 3H, 10Ac), 1.83 (m, 1H, H6$\beta$), 1.82 (br s, 3H, Me18), 1.68 (s, 1H, 10H), 1.68 (s, 3H, Me19), 1.24 (s, 3H, Me17), 1.14 (s, 3H, Me16).

EXAMPLE 3

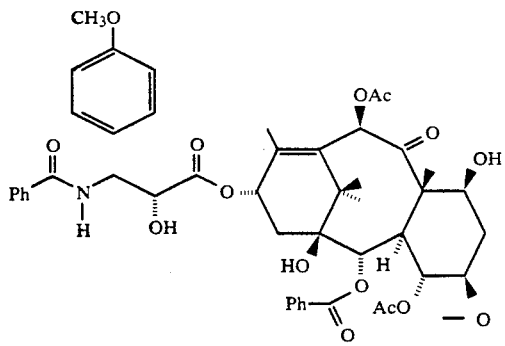

Preparation of 3'-desphenyl-3'-(4-methoxyphenyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(4-methoxyphenyl)azetidin-2-one (590 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 320 mg of a mixture containing (2'R,3'S)-2',7-(bis)triethylsilyl-3-desphenyl-3'-(4-methoxyphenyl) taxol and a small amount of the (2'S, 3'R) isomer.

To a solution of 320 mg (0.288 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 255 mg of material which was purified by flash chromatography to give 172 mg (68%) of 3'-desphenyl-3'-(4-methoxyphenyl) taxol, which was recrystallized from methanol/water.

m.p. 174°-176° C.; $[\alpha]^{25}_{Na}$ −48.86° (c 0.05, CHCl$_3$).

$^1$H NMR (CDCl$_3$, 300 MHz) $\delta$8.12 (d, J=7.1 Hz, 2H, benzoate ortho), 7.72 (m, 2H, aromatic), 7.59 (m, 1H, aromatic), 7.53-7.36 (m, 8H, aromatic), 6.96 (d, J=8.8 Hz, 1H, NH), 6.90 (m, 2H, aromatic), 6.26 (s, 1H, H10), 6.21 (dd, J=9.3, 9.3 Hz, 1H, H13), 5.70 (dd, J=8.8, 2.7 Hz, 1H, H3'), 5.66 (d, J=6.8 Hz, 1H, H2$\beta$), 4.93 (dd, J=9.9, 2.2 Hz, 1H, H5), 4.74 (dd, J=5.5, 2.7 Hz, 1H, H2'), 4.39 (m, 1H, H7), 4.29 (d, J=8.8 Hz, 1H, H20$\alpha$), 4.18 (d, J=8.8 Hz, 1H, H20$\beta$), 3.78 (d, J=6.8 Hz, 1H, H3), 3.78 (s, 3H, ArOMe), 3.67 (d, J=5.5 Hz, 1H, 2'OH), 2.61 (m, 1H, H6$\alpha$), 2.50 (d, J=4.4 Hz, 1H, 7OH), 2.37 (s, 3H, 4Ac), 2.31 (m, 2H, H14), 2.22 (s, 3H, 10Ac), 1.84 (m, 1H, H6$\beta$), 1.79 (br s, 3H, Me18), 1.79 (s, 1H, 1OH), 1.67 (s, 3H, Me19), 1.22 (s, 3H, Me17), 1.13 (s, 3H, Me16).

EXAMPLE 4

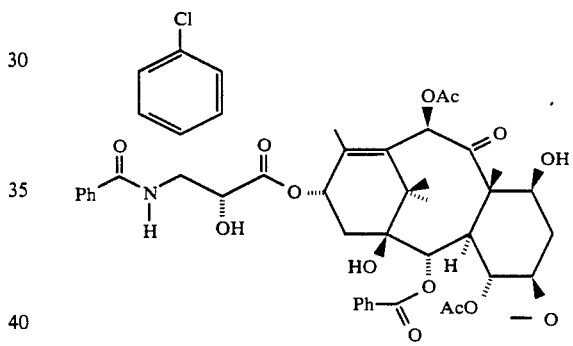

Preparation of 3'-desphenyl-3'-(4-chlorophenyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(4-chlorophenyl)azetidin-2-one (595 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 320 mg of a mixture containing (2'R,3'S)-2',7-(bis)triethylsilyl-3'-desphenyl-3'-(4-chlorophenyl) taxol and a small amount of the (2'S,3'R) isomer.

To a solution of 320 mg (0.287 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 255 mg of material which was purified by flash chromatography to give 158 mg (62%) of 3'-desphenyl-3'-(4-chlorophenyl) taxol, which was recrystallized from methanol/water.

m.p. 173°-175° C.; $[\alpha]^{25}_{Na}$ −50.8° (c 0.01, CHCl$_3$).

$^1$H NMR (CDCl$_3$, 300 MHz) δ8.13 (d, J=7.1 Hz, 2H, benzoate ortho), 7.72 (d, J=8.2 Hz, 2H, benzamide ortho), 7.65-7.35 (m, 10H, aromatic), 6.97 (d, J=8.8 Hz, 1H, NH), 6.27 (s, 1H, H10), 6.25 (dd, J=8.3, 8.3 Hz, 1H, H13), 5.78 (dd, J=8.8, 2.2 Hz, 1H, H3'), 5.67 (d, J=7.1 Hz, 1H, H2β), 4.95 (dd, J=8.8, 2.2 Hz, 1H, H5), 4.77 (br s, 1H, H2'), 4.40 (m, 1H, H7), 4.31 (d, J=8.2 Hz, 1H, H20α), 4.19 (d, J=8.2 Hz, 1H, H20β), 3.80 (d, J=7.1 Hz, 1H, H3), 3.61 (br s, 1H, 2'OH), 2.54 (m, 1H, H6α), 2.38 (s, 3H, 4Ac), 2.32 (m, 2H, H14), 2.24 (s, 3H, 10Ac), 1.85 (m, 1H, H6β), 1.80 (br s, 3H, Me18), 1.68 (s, 3H, Me19), 1.23 (s, 3H, Me17), 1.14 (s, 3H, Me16).

EXAMPLE 5

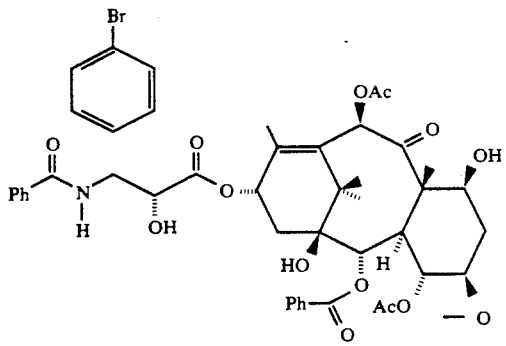

Preparation of 3'-desphenyl-3'-(4-bromophenyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(4-bromophenyl)azetidin-2-one (660 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 330 mg of a mixture containing (2'R,3'S)-2',7-(bis)triethylsilyl-3'-desphenyl-3'-(4-bromophenyl) taxol and a small amount of the (2'S,3'R) isomer.

To a solution of 330 mg (0.284 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 265 mg of material which was purified by flash chromatography to give 186 mg (64%) of 3'-desphenyl-3'-(4-bromophenyl) taxol, which was recrystallized from methanol/water.

m.p. 170°-172° C.; $[\alpha]^{25}_{Na}$ −50.94° (c 0.01, CHCl$_3$).

$^1$H NMR (CDCl$_3$, 300 MHz) δ8.12 (d, J=7.2 Hz, 2H, benzoate ortho), 7.71 (m, 2H, aromatic), 7.61 (m, 1H, aromatic), 7.50-7.47 (m, 6H, aromatic), 7.38 (m, 3H, aromatic), 7.04 (d, J=8.8 Hz, 1H, NH), 6.27 (s, 1H, H10), 6.23 (dd, J=8.2, 8.2 Hz, 1H, H13), 5.75 (dd, J=8.8, 2.2 Hz, 1H, H3'), 5.66 (d, J=7.1 Hz, 1H, H2β), 4.94 (dd, J=9.3, 1.7 Hz, 1H, H5), 4.75 (dd, J=2.2 Hz, 1H, H2'), 4.38 (m, 1H, H7), 4.29 (d, J=8.2 Hz, 1H, H20α), 4.18 (d, J=8.2 Hz, 1H, H20β), 3.79 (d, J=7.1 Hz, 1H, H3), 3.7 (br, 1H, 2'OH), 2.53 (m, 1H, H6α), 2.38 (br, 1H, 7OH), 2.37 (s, 3H, 4Ac), 2.30 (m, 2H, H14), 2.23 (s, 3H, 10Ac), 1.87 (m, 1H, H6β), 1.80 (br s, 3H, Me18), 1.80 (s, 1H, 1OH), 1.67 (s, 3H, Me19), 1.22 (s, 3H, Me17), 1.13 (s, 3H, Me16).

EXAMPLE 6

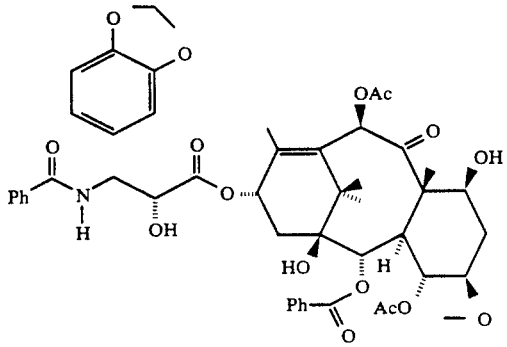

Preparation of 3'-desphenyl-3'-(3,4-methylenedioxyphenyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(3,4-methylenedioxyphenyl)azetidin-2-one (610 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 320 mg of a mixture containing (2'R,3'S)-2',7-(bis)triethylsilyl-3'-desphenyl-3'-(3,4-methylenedioxyphenyl) taxol and a small amount of the (2'S,3'R) isomer.

To a solution of 320 mg (0.284 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 113 mg of material which was purified by flash chromatography to give 165 mg (64%) of 3'-desphenyl-3'-(3,4-methylenedioxyphenyl) taxol, which was recrystallized from methanol/water.

m.p. 178°-180° C.; $[\alpha]^{25}_{Na}$ −46.6° (c 0.005, CHCl$_3$).

$^1$H NMR (CDCl$_3$, 300 MHz) δ8.14 (d, J=7.2 Hz, 2H, benzoate ortho), 7.72 (m, 2H, aromatic), 7.15 (m, 1H, aromatic), 7.50 (m, 2H, aromatic), 7.38 (m, 2H, aromatic), 7.0 (m, 1H, aromatic), 6.94 (m, 2H, aromatic), 6.88 (d, J=9.1 Hz, 1H, NH), 6.83 (m, 1H, aromatic), 6.28 (s, 1H, H10), 6.23 (dd, J=9.1, 9.1 Hz, 1H, H13), 5.97 (s, 2H, methylene), 5.69 (dd, J=9.1, 2.5 Hz, 1H, H3'), 5.68 (d, J=6.9 Hz, 1H, H2β), 4.95 (dd, J=9.6, 2.2 Hz, 1H, H5), 4.72 (dd, J=2.5 Hz, 1H, H2'), 4.41 (m, 1H, H7), 4.31 (d, J=8.4 Hz, 1H, H20α), 4.20 (d, J=8.4 Hz, 1H, H20β), 3.81 (d, J=6.9 Hz, 1H, H3), 3.60 (br, 1H, 2'OH), 2.56 (m, 1H, H6α), 2.43 (d, J=4.1 Hz, 1H, 7OH), 2.39 (s, 3H, 4Ac), 2.31 (m, 2H, H14), 2.24 (s, 3H, 10Ac), 1.88 (m, 1H, H6β), 1.82 (br s, 3H, Me18), 1.69 (s, 1H, 1OH), 1.68 (s, 3H, Me19), 1.24 (s, 3H, Me17), 1.15 (s, 3H, Me16).

EXAMPLE 7

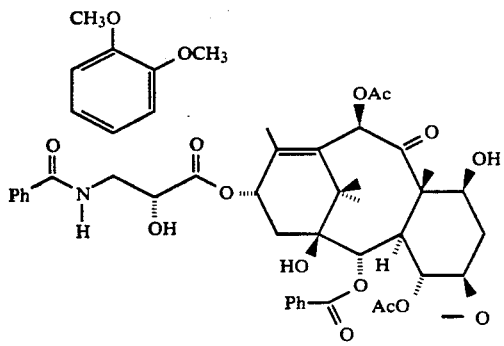

Preparation of 3'-desphenyl-3'-(3,4-dimethoxyphenyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(3,4-dimethoxyphenyl)azetidin-2-one (630 mg, 1.43 mmol) in 2 mL of THF was added dropwise to the mixture. The solution was warmed to 0° C. and kept at that temperature for 1 h before 1 mL of A 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 330 mg of a mixture containing (2'R, 3'S)-2',7-(bis)triethylsilyl-3'-desphenyl-3'-(3,4-dimethoxyphenyl) taxol and a small amount of the (2'S,3'R) isomer.

To a solution of 330 mg (0.286 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 260 mg of material which was purified by flash chromatography to give 175 mg (67%) of 3'-desphenyl-3'-(3,4-dimethoxyphenyl) taxol, which was recrystallized from methanol/water.

m.p. 165°-167° C.; [α]25Na −42.0° (c 0.005, CHCl3).

1H NMR (CDCl3, 300 MHz) δ8.12 (d, J=8.3 Hz, 2H, benzoate ortho), 7.73 (d, J=8.2 Hz, 2H, benzamide ortho), 7.65-7.35 (m, 6H, aromatic), 7.1-7.0 (m, 2H, aromatic), 6.94 (d, J=8.8 Hz, 1H, NH), 6.88 (d, J=8.3 Hz, 2H, aromatic), 6.27 (s, 1H, H10), 6.21 (dd, J=9.3, 9.3 Hz, 1H, H13), 5.69 (m, 2H, H3, H2β), 4.94 (dd, Hz, J=9.9, 2.2 Hz, 1H, H5), 4.77 (d, J=2.8 Hz, 1H, H2'), 4.39 (dd, J=11.0, 6.6 Hz, 1H, H7), 4.30 (d, J=8.5 Hz, 1H, H20α), 4.19 (d, J=8.5 Hz, 1H, H20β), 3.88 (s, 3H, ArOMe), 3.87 (s, 3H, ArOMe), 3.80 (d, J=7.1 Hz, 1H, H3), 3.59 (d, J=4.4 Hz, 1H, 2'OH), 2.54 (m, 1H, H6α), 2.38 (s, 3H, 4Ac), 2.36 (m, 2H, H14α, H14β), 2.23 (s, 3H, 10Ac), 1.86 (m, 1H, H6β), 1.80 (br s, 3H, Me18), 1.68 (s, 3H, Me19), 1.23 (s, 3H, Me17), 1.14 (s, 3H, Me16).

EXAMPLE 8

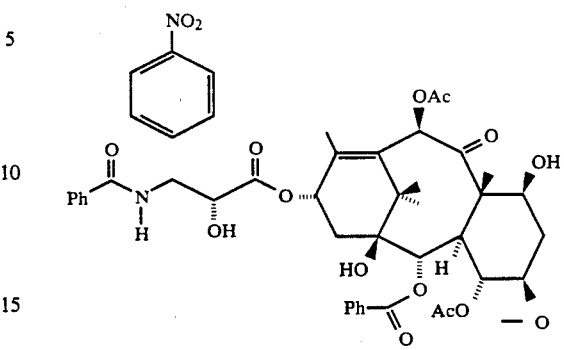

Preparation of 3'-desphenyl-3'-(4-nitrophenyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(4-nitrophenyl)azetidin-2-one (610 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 320 mg of a mixture containing (2'R,3'S)-2',7-(bis)triethylsilyl-3'-desphenyl-3'-(4-nitrophenyl) taxol and a small amount of the (2'S,3'R) isomer.

To a solution of 320 mg (0.284 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 255 mg of material which was purified by flash chromatography to give 147 mg (57%) of 3'-desphenyl-3'-(4-nitrophenyl) taxol, which was recrystallized from methanol/water.

m.p. 188°-190° C.; [α]25Na −63.7° (c 0.01, CHCl3).

1H NMR (CDCl3, 300 MHz) δ8.26 (d, J=8.8 Hz, 2H, benzoate ortho), 8.20 (m, 2H, aromatic), 7.73 (m, 4H, aromatic), 7.60 (m, 1H, aromatic), 7.52 (m, 4H, aromatic), 7.41 (m, 1H, aromatic), 7.15 (d, J=8.8 Hz, 1H, NH), 6.26 (s, 1H, H10), 6.26 (dd, J=9.3, 9.3 Hz, 1H, H13), 5.93 (dd, J=8.8, 2.8 Hz, 1H, H3'), 5.66 (d, J=6.6 Hz, 1H, H2β), 4.94 (dd, J=9.3, 1.7 Hz, 1H, H5), 4.82 (dd, J=3.9, 2.8 Hz, 1H, H2'), 4.38 (m, 1H, H7), 4.30 (d, J=8.8 Hz, 1H, H20α), 4.19 (d, J=8.8 Hz, 1H, H20β), 3.86 (d, J=3.9 Hz, 1H, 2'OH), 3.79 (d, J=6.6 Hz, 1H, H3), 2.55 (m, 1H, H6α), 2.46 (d, J=3.8 Hz, 1H, 7OH), 2.41 (s, 3H, 4Ac), 2.38 (m, 2H, H14), 2.23 (s, 3H, 10Ac), 1.82 (m, 1H, H6β), 1.80 (br s, 3H, Me18), 1.74 (s, 1H, 1OH), 1.68 (s, 3H, Me19), 1.21 (s, 3H, Me17), 1.13 (s, 3H, Me16).

EXAMPLE 9

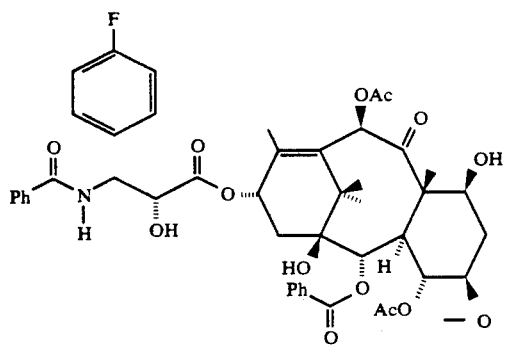

Preparation of 3'-desphenyl-3'-(4-fluorophenyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-benzoyl-3-triethylsilyloxy-4-(4-fluorophenyl)azetidin-2-one (570 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 315 mg of a mixture containing (2'R,3'S)-2',7-(bis)triethylsilyl-3'-desphenyl-3'-(4-fluorophenyl) taxol and a small amount of the (2'S,3'R) isomer.

To a solution of 315 mg (0.286 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 250 mg of material which was purified by flash chromatography to give 160 mg (64%) of 3'-desphenyl-3'-(4-fluorophenyl) taxol, which was recrystallized from methanol/water.

m.p.171°-173° C.;$[\alpha]^{25}_{Na}$ −49.0° (c 0.005, $CHCl_3$).

$^1$H NMR ($CDCl_3$, 300 MHz) δ8.13 (d, J=7.5 Hz, 2H, benzoate ortho), 7.25 (m, 2H, aromatic), 7.61 (m, 1H, aromatic), 7.50 (m, 4H, aromatic), 7.43 (m, 2H, aromatic), 7.10 (m, 2H, aromatic), 6.96 (d, J=8.7 Hz, 1H, NH), 6.27 (s, 1H, H10), 6.25 (dd, J=8.7, 8.7 Hz, 1H, H13), 5.79 (dd, J=8.7, 2.4 Hz, 1H, H3'), 5.67 (d, J=7.1 Hz, 1H, H2β), 4.45 (dd, J=7.9 Hz, 1H, H5), 4.76 (dd, J=4.8, 2.4 Hz, 1H, H2'), 4.39 (m, 1H, H7), 4.31 (d, J=8.9 Hz, 1H, H20α), 4.20 (d, J=8.9 Hz, 1H, H20β), 3.80 (d, J=7.1 Hz, 1H, H3), 3.57 (d, J=4.8 Hz, 1H, 2'OH), 2.58 (m, 1H, H6a), 2.43 (d, J=4.3 Hz, 1H, 7OH), 2.38 (s, 3H, 4Ac), 2.30 (m, 2H, H14), 2.24 (s, 3H, 10Ac), 1.85 (m, 1H, H6β), 1.80 (br s, 3H, Me18), 1.69 (s, 1H, 10H), 1.55 (s, 3H, Me19), 1.23 (s, 3H, Me17), 1.14 (s, 3H, Me16).

EXAMPLE 10

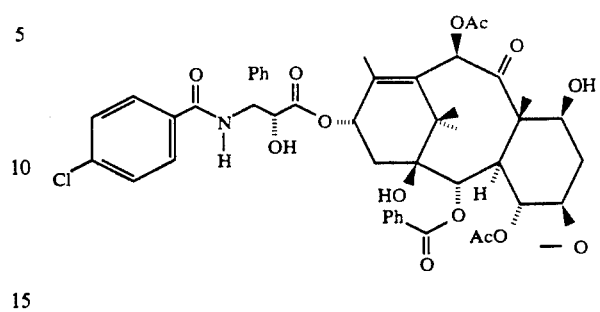

Preparation of N-debenzoyl-N-(4-chlorobenzoyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of (+)-cis-1-(4-chlorobenzoyl)-3-triethylsilyloxy-4-phenylazetidin-2-one (215 mg, 0.515 mmol) in 2 mL of THF was added dropwise to the mixture. The solution was warmed to 0° C. and kept at that temperature for 2 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 320 mg of crude (2'R,3'S)-2',7-(bis)triethylsilyl-N-debenzoyl-N-(4-chlorobenzoyl) taxol.

To a solution of 320 mg (0.286 mmol) of this crude product in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 252 mg of material which was purified by flash chromatography to give 213 mg (84%) of N-debenzoyl-N-(4-chlorobenzoyl) taxol, which was recrystallized from methanol/water.

m.p. 179°-181° C.; $[\alpha]^{25}_{Na}$ −49.8° (c 0.01, $CHCl_3$). $^1$H NMR ($CDCl_3$, 300 MHz) δ8.12 (d, J=7.1 Hz, 2H, benzoate ortho), 7.64 (m, 2H, aromatic), 7.60 (m, 1H, aromatic), 7.49 (m, 9H, aromatic), 7.03 (d, J=8.8 Hz, 1H, NH), 6.26 (s, 1H, H10), 6.21 (dd, J=8.2, 8.2 Hz, 1H, H13), 5.76 (dd, J=8.8, 2.2 Hz, 1H, H3'), 5.66 (d, J=7.1 Hz, 1H, H2β), 4.92 (dd, J=9.9, 1.1 Hz, 1H, H5), 4.77 (dd, J=5.5, 2.2 Hz, 1H, H2'), 4.38 (m, 1H, H7), 4.29 (d, J=8.8 Hz, 1H, H20α), 4.18 (d, J=8.5 Hz, 1H, H20β), 3.78 (d, J=6.6 Hz, 1H, H3), 3.35 (d, J=5.5 Hz, 1H, 2'OH), 2.55 (m, 1H, H6α), 2.49 (d, J=4.2 Hz, 1H, 7OH), 2.36 (s, 3H, 4Ac), 2.28 (m, 2H, H14), 2.22 (s, 3H, 10Ac), 1.85 (m, 1H, H6β), 1.77 (br s, 3H, Me18), 1.76 (s, 1H, 10H), 1.67 (s, 3H, Me19), 1.22 (s, 3H, Me17), 1.13 (s, 3H, Me16).

EXAMPLE 11

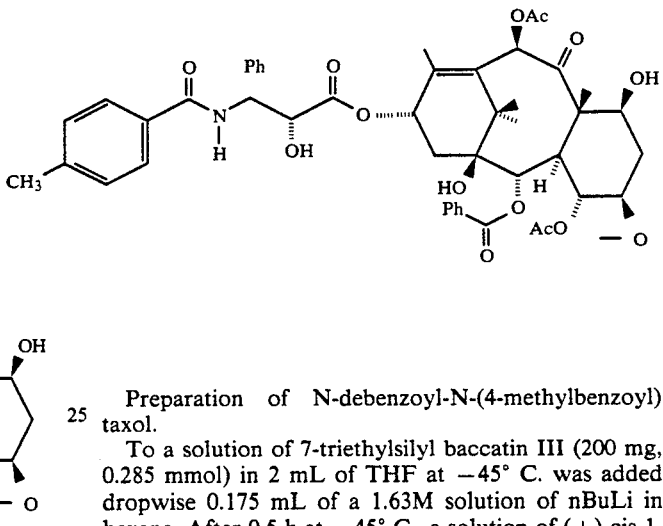

Preparation of N-debenzoyl-N-(4-bromobenzoyl) taxol.

To a solution of 7-triethylsilyl baccatin III (200 mg, 0.285 mmol) in 2 mL of THF at −45° C. was added dropwise 0.175 mL of a 1.63M solution of nBuLi in hexane. After 0.5 h at −45° C., a solution of (+)-cis-1-(4-bromobenzoyl)-3-triethylsilyloxy-4-phenylazetidin-2-one (236 mg, 0.513 mmol) in 2 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 322 mg of crude (2'R,3'S)-2',7-(bis)triethylsilyl-N-debenzoyl-N-(4-bromobenzoyl) taxol.

To a solution of 322 mg of this crude product in 12 mL of acetonitrile and 0.6 mL of pyridine at 0° C. was added 1.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 312.2 mg of material which was purified by flash chromatography to give 254 mg (96%) of N-debenzoyl-N-(4-bromobenzoyl) taxol, which was recrystallized from methanol/water.

m.p. 182.5°–185° C.; $[\alpha]^{25}_{Na}$ −47.8° (c 0.0051, CHCl$_3$).

$^1$H NMR (CDCl$_3$, 300 MHz) δ8.14 (d, J=7.1 Hz, 2H, benzoate ortho), 7.7–7.3 (m, 12H, aromatic), 6.96 (d, J=8.8 Hz, 1H, NH), 6.27 (s, 1H, H10), 6.22 (dd, J=9.1, 9.1 Hz, 1H, H13), 5.77 (dd, J=8.8, 2.2 Hz, 1H, H3'), 5.67 (d, J=7.2 Hz, 1H, H2b), 4.94 (dd, J=9.9, 2.2 Hz, 1H, H5), 4.78 (dd, J=5.0, 2.7 Hz, 1H, H2'), 4.40 (m, 1H, H7), 4.30 (d, J=8.5 Hz, 1H, H20α), 4.19 (d, J=8.5 Hz, 1H, H20β), 3.79 (d, J=7.2 Hz, 1H, H3), 3.48 (d, J=5.0 Hz, 1H, 2'OH), 2.54 (m, 1H, H6α), 2.45 (d, J=4.4 Hz, 1H, 7OH), 2.37 (s, 3H, 4Ac), 2.30 (m, 2H, H14α, H14β), 2.24 (s, 3H, 10Ac), 1.88 (m, 1H, H6β), 1.78 (br s, 3H, Me18), 1.68 (s, 3H, Me19), 1.24 (s, 3H, Me17), 1.14 (s, 3H, Me16).

EXAMPLE 12

Preparation of N-debenzoyl-N-(4-methylbenzoyl) taxol.

To a solution of 7-triethylsilyl baccatin III (200 mg, 0.285 mmol) in 2 mL of THF at −45° C. was added dropwise 0.175 mL of a 1.63M solution of nBuLi in hexane. After 0.5 h at −45° C., a solution of (+)-cis-1-(4-methylbenzoyl)-3-triethylsilyloxy-4-phenylazetidin-2-one (203 mg, 0.513 mmol) in 2 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 386 mg of crude (2'R,3'S)-2',7-(bis)triethylsilyl-N-debenzoyl-N-(4-methylbenzoyl) taxol.

To a solution of 386 mg of this crude product in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 283 mg of material which was purified by flash chromatography to give 240 mg (97%) of N-debenzoyl-N-(4-methylbenzoyl) taxol, which was recrystallized from methanol/water.

m.p. 175°–176.5° C.; $[\alpha]^{25}_{Na}$ −50.9° (c 0.00975, CHCl$_3$).

$^1$H NMR (CDCl$_3$, 300 MHz) δ8.13 (d, J=7.1 Hz, 2H, benzoate ortho), 7.7–7.3 (m, 10H, aromatic), 7.19 (d, J=7.7 Hz, 2H, benzoate meta), 6.94 (d, J=8.8 Hz, 1H, NH), 6.27 (s, 1H, H10), 6.22 (dd, J=9.3, 9.3 Hz, 1H, H13), 5.77 (dd, J=9.3, 2.8 Hz, 1H, H3'), 5.67 (d, J=7.2 Hz, 1H, H2b), 4.94 (dd, J=9.9, 2.2 Hz, 1H, H5), 4.78 (dd, J=4.9, 2.8 Hz, 1H, H2'), 4.42 (m, 1H, H7), 4.30 (d, J=8.5 Hz, 1H, H20a), 4.19 (d, J=8.5 Hz, 1H, H20b), 3.79 (d, J=7.2 Hz, 1H, H3), 3.60 (d, J=4.9 Hz, 1H, 2'OH), 2.53 (m, 1H, H6a), 2.46 (d, J=4.4 Hz, 1H, 7OH), 2.38 (s, 3H, 4Ac), 2.37 (s, 3H, ArMe), 2.31 (m, 2H, H14a, H14b), 2.23 (s, 3H, 10Ac), 1.87 (m, 1H, H6b), 1.78 (br s, 3H, Me18), 1.68 (s, 3H, Me19), 1.23 (s, 3H, Me17), 1.14 (s, 3H, Me16).

EXAMPLE 13

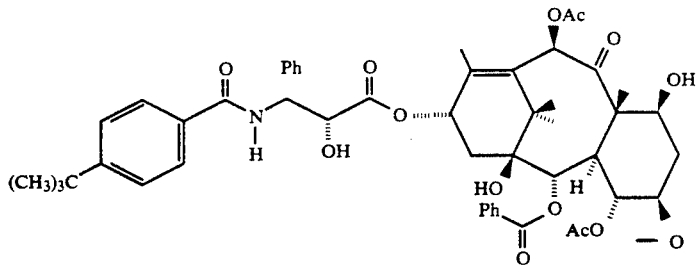

Preparation of N-debenzoyl-N-(4-t-butylbenzoyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of (+)-cis-1-(4-t-butylbenzoyl)-3-triethylsilyloxy-4-phenylazetidin-2-one (226 mg, 0.515 mmol) in 2 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 330 mg of crude (2'R,3'S)-2',7-(bis)triethylsilyl-N-debenzoyl-N-(4-t-butylbenzoyl) taxol.

To a solution of 330 mg (0.289 mmol) of this crude product in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 260 mg of material which was purified by flash chromatography to give 240 mg (92%) of N-debenzoyl-N-(4-t-butylbenzoyl) taxol, which was recrystallized from methanol/water. m.p. 171°–173° C.; $[\alpha]^{25}_{Na}$ −49.1° (c 0.05, CHCl3).

$^{1}$H NMR (CDCl3, 300 MHz) δ8.13 (d, J=7.1 Hz, 2H, benzoate ortho), 7.76–7.25 (m, 12H, aromatic), 6.98 (d, J=8.8 Hz, 1H, NH), 6.27 (s, 1H, H10), 6.21 (dd, J=8.8, 8.8 Hz, 1H, H13), 5.77 (dd, J=8.8, 2.7 Hz, 1H, H3'), 5.67 (d, J=6.6 Hz, 1H, H2β), 4.94 (dd, J=9.3, 1.2 Hz, 1H, H5), 4.78 (dd, J=4.4, 2.7 Hz, 1H, H2'), 4.38 (m, 1H, H7), 4.29 (d, J=8.2 Hz, 1H, H20α), 4.20 (d, J=8.2 Hz, 1H, H20β), 3.79 (d, J=6.6 Hz, 1H, H3), 3.65 (d, J=4.4 Hz, 1H, 2'OH), 2.57 (m, 1H, H6α), 2.48 (d, J=4.1 Hz, 1H, 7OH), 2.37 (s, 3H, 4Ac), 2.31 (m, 2H, H14), 2.22 (s, 3H, 10Ac), 1.85 (m, 1H, H6β), 1.79 (br s, 3H, Me18), 1.68 (s, 1H, 10H), 1.68 (s, 3H, Me19), 1.29 (s, 9H, Ar'Bu), 1.23 (s, 3H, Me17), 1.13 (s, 3H, Me16).

EXAMPLE 14

Preparation of N-debenzoyl-N-(4-methoxybenzoyl) taxol.

To a solution of 7-triethylsilyl baccatin III (200 mg, 0.285 mmol) in 2 mL of THF at −45° C. was added dropwise 0.175 mL of a 1.63M solution of nBuLi in hexane. After 0.5 h at −45° C., a solution of (+)-cis-1-(4-methoxybenzoyl)-3-triethylsilyloxy-4-phenylazetidin-2-one (211 mg, 0.513 mmol) in 2 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 406 mg of crude (2'R,3'S)-2',7-(bis)triethylsilyl-N-debenzoyl-N-(4-methoxybenzoyl) taxol.

To a solution of 406 mg (0.112 mmol) of this crude product in 12 mL of acetonitrile and 0.6 mL of pyridine at 0° C. was added 1.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 308 mg of material which was purified by flash chromatography to give 236 mg (94%) of N-debenzoyl-N-(4-methoxybenzoyl) taxol, which was recrystallized from methanol/water. m.p. 174.5°–176° C.; $[\alpha]^{25}_{Na}$ −49.5° (c 0.0084, CHCl3).

$^{1}$H NMR (CDCl3, 300 MHz) δ8.13 (d, J=7.1 Hz, 2H, benzoate ortho), 7.75–7.3 (m, 10H, aromatic), 6.90 (d, J=8.2 Hz, 1H, NH), 6.88 (d, J=7.1 Hz, 2Hz, 2H, benzoate meta), 6.27 (s, 1H, H10), 6.22 (dd, J=8.8, 8.8 Hz, 1H, H13), 5.76 (dd, J=8.8, 2.7 Hz, 1H, H3'), 5.67 (d, J=7.1 Hz, 1H, H2), 4.94 (dd, J=9.9, 2.2 Hz, 1H, H5), 4.78 (d, J=2.7 Hz, 1H, H2'), 4.40 (dd, J=11.0, 7.1 Hz, 1H, H7), 4.30 (d, J=8.5 Hz, 1H, H20α), 4.19 (d, J=8.5 Hz, 1H, H20β), 3.82 (s, 3H, OMe), 3.79 (d, J=7.1 Hz, 1H, H3), 2.55 (m, 1H, H6α), 2.38 (s, 3H, 4Ac), 2.30 (m, 2H, H14α, H14β), 2.23 (s, 3H, 10Ac), 1.87 (m, 1H, H6β), 1.78 (br s, 3H, Me18), 1.68 (s, 3H, Me19), 1.23 (s, 3H, Me17), 1.14 (s, 3H, Me16).

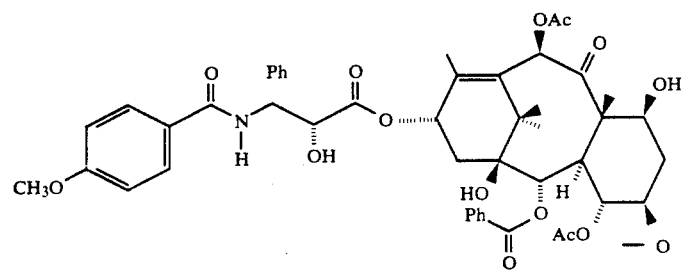

EXAMPLE 15

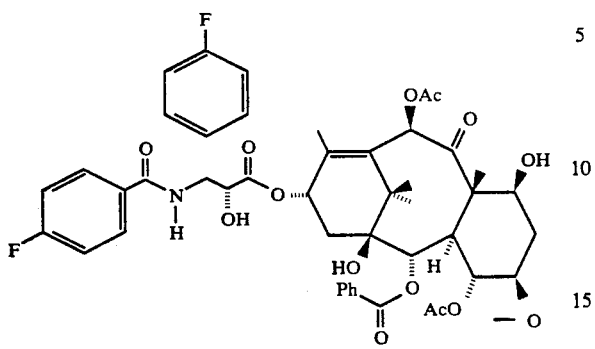

Preparation of N-debenzoyl-N-(4-fluorobenzoyl)-3'-desphenyl-3'-(4-fluorophenyl) taxol.

To a solution of 7-triethylsilyl baccatin III (200 mg, 0.286 mmol) in 2 mL of THE at −45° C. was added dropwise 0.174 mL of a 1.63M solution of nBuLi in hexane. After 0.5 h at −45° C., a solution of cis-1-(4-fluorobenzoyl)-3-triethylsilyloxy-4-(4-fluorophenyl)azetidin-2-one (600 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 315 mg of a mixture containing (2'R,3'S)-2',7-(bis)triethylsilyl-N-debenzoyl-N-(4-fluorobenzoyl)-3'-desphenyl-3'-(4-fluorophenyl) taxol and a small amount of the (2'S,3'R) isomer.

To a solution of 315 mg (0.282 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 250 mg of material which was purified by flash chromatography to give 160 mg (63%) of N-debenzoyl-N-(4-fluorobenzoyl)-3'-desphenyl-3'-(4-fluorophenyl) taxol, which was recrystallized from methanol/water.

m.p. 177°-179° C.; $[\alpha]^{25}_{Na}$ −48.8° (c 0.003, CHCl3).

1H NMR (CDCl3, 300 MHz) δ8.11 (d, J=7.1 Hz, 2H, benzoate ortho), 7.76 (d, J=8.7 Hz, 2H, benzamide ortho), 7.73 (m, 2H, aromatic), 7.61 (m, 1H, aromatic), 7.48 (m, 6H, aromatic), 7.06 (m, 2H, aromatic), 7.02 (d, J=8.8 Hz, 1H, NH), 6.26 (s, 1H, H10), 6.22 (dd, J=8.8, 8.8 Hz, 1H, H13), 5.74 (dd, J=8.8, 2.2 Hz, 1H, H3'), 5.66 (d, J=7.1 Hz, 1H, H2β), 4.93 (dd, J=9.3, 1.1 Hz, 1H, H5), 4.74 (dd, J=5.0, 2.2 Hz, 1H, H2'), 4.36 (m, 1H, H7), 4.29 (d, J=8.8 Hz, 1H, H20α), 4.18 (d, J=8.8 Hz, 1H, H20β), 3.77 (d, J=7.1 Hz, 1H, H3), 3.70 (d, J=5.0 Hz, 1H, 2'OH), 2.77 (m, 1H, H6α), 2.52 (d, J=4.4 Hz, 1H, 7OH), 2.3 (s, 3H, 4Ac), 2.30 (m, 2H, H14), 2.22 (s, 3H, 10Ac), 1.86 (m, 1H, H6β), 1.78 (br s, 3H, Me18), 1.77 (s, 1H, 1OH), 1.67 (s, 3H, Me19), 1.21 (s, 3H, Me17), 1.13 (s, 3H, Me16).

EXAMPLE 16

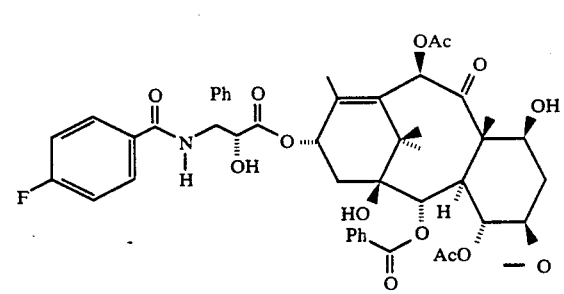

Preparation of N-debenzoyl-N-(4-fluoroobenzoyl) taxol.

To a solution of 7-triethylsilyl baccatin III (200 mg, 0.286 mmol)) in 2 mL of THF at −45° C. was added dropwise 0.174 mL of a 1.63M solution of nBuLi in hexane. After 0.5 h at −45° C., a solution of (+)-cis-1-(4-fluorobenzoyl)-3-triethylsilyloxy-4-phenylazetidin-2-one (225 mg, 0.515 mmol) in 2 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 325 mg of crude (2'R,3'S)-2',7-(bis)triethylsilyl-N-benzoyl-N-(4-fluorobenzoyl) taxol.

To a solution of 325 mg (0.286 mmol) of this crude product in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 260 mg of material which was purified by flash chromatography to give 240 mg (92%) of N-debenzoyl-N-(4-fluorobenzoyl) taxol, which was recrystallized from methanol/water.

m.p. 175°-177° C.; $[\alpha]^{25}_{Na}$ −51.2° (c 0.01, CHCl3).

1H NMR (CDCl3, 300 MHz) δ8.13 (d, J=7.1 Hz, 2H, benzoate ortho), 7.74 (m, 2H, aromatic), 7.62 (m, 2H, aromatic), 7.46 (m, 6H, aromatic), 7.06 (m, 2H, aromatic), 6.95 (d, J=8.8 Hz, 1H, NH), 6.28 (s, 1H, H10), 6.22 (dd, J=8.2, 8.2 Hz, 1H, H13), 5.76 (dd, J=8.8, 2.8 Hz, 1H, H3'), 5.67 (d, J=7.1 Hz, 1H, H2β), 4.93 (dd, J=9.9, 2.2 Hz, 1H, H5), 4.78 (dd, J=5.5, 2.8 Hz, 1H, H2'), 4.39 (m, 1H, H7), 4.30 (d, J=8.8 Hz, 1H, H20α), 4.22 (d, J=8.8 Hz, 1H, H20β), 3.79 (d, J=7.1 Hz, 1H, H3), 3.54 (d, J=5.5 Hz, 1H, 2'OH), 2.54 (m, 1H, H6α), 2.46 (d, J=4.4 Hz, 1H, 7OH), 2.37 (s, 3H, 4Ac), 2.30 (m, 2H, H14), 2.26 (s, 3H, 10Ac), 1.87 (m, 1H, H6β), 1.79 (br s, 3H, Me18), 1.79 (s, 1H, 1OH), 1.67 (s, 3H, Me19), 1.24 (s, 3H, Me17), 1.12 (s, 3H, Me16).

EXAMPLE 17

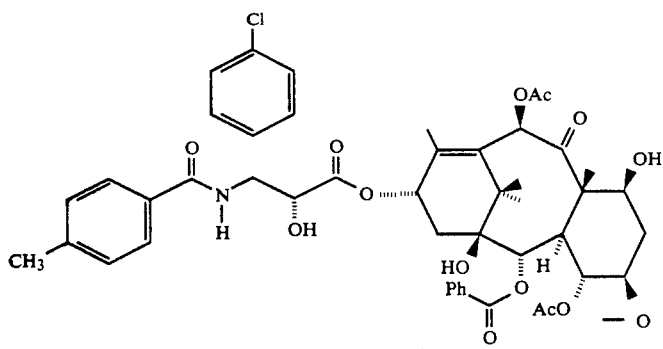

EXAMPLE 18

20

Preparation of N-debenzoyl-N-(4-methylbenzoyl)-3'-desphenyl-3'-(4-chlorophenyl) taxol.

To a solution of 7-triethylsilyl baccatin III (200 mg, 0.285 mmol) in 2 mL of THF at −45° C. was added dropwise 0.175 mL of a 1.63M solution of nBuLi in hexane. After 0.5 h at −45° C., a solution of cis-1-(4-methylbenzoyl)-3-triethylsilyloxy-4-(4-chlorophenyl-)azetidin-2-one (718 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 329 mg of a mixture containing (2'R,3'S)-2',7-(bis)triethylsilyl-N-debenzoyl-N-(4-methylbenzoyl)-3'-desphenyl-3'-(4-chlorophenyl) taxol and a small amount of the (2'S,3'R) isomer.

To a solution of 329 mg of the mixture obtained from the previous reaction in 12 mL of acetonitrile and 0.6 mL of pyridine at 0° C. was added 1.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 376 mg of material which was purified by flash chromatography to give 175 mg (68%) of N-debenzoyl-N-(4-methylbenzoyl)-3'-desphenyl-3'-(4-chlorophenyl) taxol, which was recrystallized from methanol/water.

m.p. 167.5°-171° C.;[α]$^{25}_{Na}$ −53.7° (c 0.01105, CHCl₃).

¹H NMR (CDCl₃, 300 MHz) δ8.12 (d, J=8.2 Hz, 2H, benzoate ortho), 7.65-7.3 (m, 9H, aromatic), 7.19 (d, J=8.2 Hz, 2H, benzoate meta), 6.97 (d, J=8.8 Hz, 1H, NH), 6.27 (s, 1H, H10), 6.22 (dd, J=9.9, 9.9 Hz, 1H, H13), 5.76 (dd, J=8.8, 2.2 Hz, 1H, H3'), 5.67 (d, J=7.1 Hz, 1H, H2β), 4.94 (dd, J=9.9, 2.2 Hz, 1H, H5), 4.76 (dd, J=4.4, 2.2 Hz, 1H, H2'), 4.39 (m, 1H, H7), 4.30 (d, J=8.8 Hz, 1H, H20α), 4.19 (d, J=8.8 Hz, 1H, H20β), 3.79 (d, J=7.1 Hz, 1H, H3), 3.75 (d, J=4.4 Hz, 1H, 2'OH), 2.54 (m, 1H, H6α), 2.49 (d, J=4.4 Hz, 1H, 7OH), 2.38 (s, 3H, 4Ac), 2.37 (s, 3H, ArMe), 2.31 (m, 2H, H14α, H14β), 2.23 (s, 3H, 10Ac), 1.87 (m, 1H, H6α), 1.80 (br s, 3H, Me18), 1.68 (s, 3H, Me19), 1.22 (s, 3H, Me17), 1.13 (s, 3H, Me16).

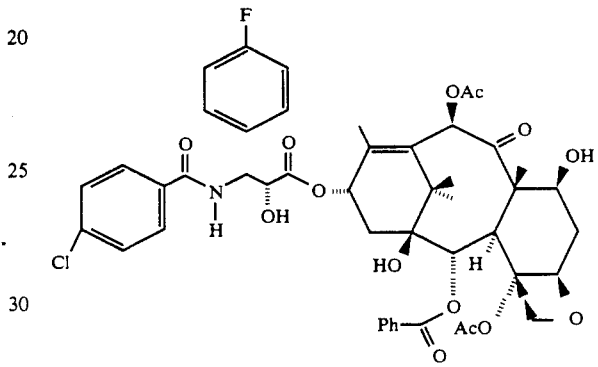

Preparation of N-debenzoyl-N-(4-chlorobenzoyl)-3'-desphenyl-3'-(4-fluorophenyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-(4-chlorobenzoyl)-3-triethylsilyloxy-4-(4-fluorophenyl-)azetidin-2-one (630 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 330 mg of a mixture containing (2'R,3'S)-2',7-(bis)triethylsilyl-N-debenzoyl-N-(4-chlorobenzoyl)-3'-desphenyl-3'-(4-fluorophenyl) taxol and a small amount of the (2'S,3'R) isomer.

To a solution of 330 mg (0.283 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 250 mg of material which was purified by flash chromatography to give 166 mg (65%) of N-debenzoyl-N-(4-chlorobenzoyl)-3'-desphenyl-3'-(4-fluorophenyl) taxol, which was recrystallized from methanol/water.

m.p. 178°-179° C.; [α]$^{25}_{Na}$ −51.9° (c 0.01, CHCl₃).

¹H NMR (CDCl₃, 300 MHz) δ8.13 (d, J=7.1 Hz, 2H, benzoate ortho), 7.64 (m, 3H, aromatic), 7.49 (m, 4H, aromatic), 7.36 (m, 2H, aromatic), 7.10 (m, 2H, aromatic), 6.97 (d, J=8.8 Hz, 1H, NH), 6.27 (s, 1H, H10), 6.21 (dd, J=8.8, 8.8 Hz, 1H, H13), 5.76 (dd, J=8.8, 2.2 Hz, 1H, H3'), 5.67 (d, J=7.2 Hz, 1H, H2β), 4.94 (dd, J=9.3, 2.2 Hz, 1H, H5), 4.75 (dd, J=4.4, 2.2 Hz, 1H, H2'), 4.39 (ddd, J=11.0, 6.6, 3.9 Hz, 1H, H7), 4.30 (d, J=8.8 Hz, 1H, H20α), 4.19 (d, J=8.8 Hz, 1H, H20β), 3.79 (d, J=7.2 Hz, 1H, H3), 3.60 (d, J=4.4 Hz, 1H, 2'OH), 2.54 (m, 1H, H6α), 2.47 (d, J=3.9 Hz, 1H, 7OH), 2.38 (s, 3H, 4Ac), 2.30 (m, 2H, H14), 2.28 (s, 3H, 10Ac), 1.87 (m, 1H, H6β), 1.78 (br s, 3H, Me18), 1.78 (s, 1H, 1OH), 1.68 (s, 3H, Me19), 1.23 (s, 3H, Me17), 1.14 (s, 3H, Me16).

EXAMPLE 19

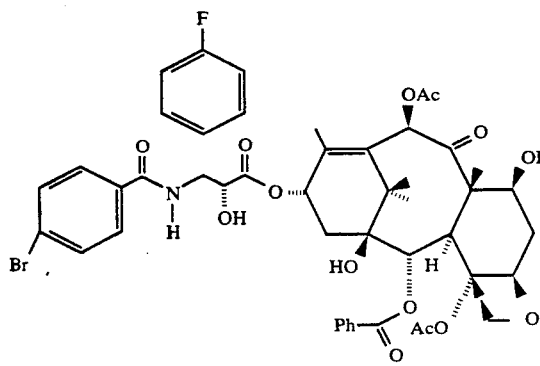

Preparation of N-debenzoyl-N-(4-bromobenzoyl)-3'-desphenyl-3'-(4-fluorophenyl) taxol.

To a solution of 7-triethylsilyl baccatin III (200 mg, 0.285 mmol) in 2 mL of THF at −45° C. was added dropwise 0.087 mL of a 1.63M solution of nBuLi in hexane. After 0.5 h at −45° C., a solution of cis-1-(4-bromobenzoyl)-3-triethylsilyloxy-4-(4-fluorophenyl)azetidin-2-one (684 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 433 mg of a mixture containing (2'R,3'S)-2',7-(bis)triethylsilyl-N-debenzoyl-N-(4-bromobenzoyl)-3'-desphenyl-3'-(4-fluorophenyl) taxol and a small amount of the (2'S,3'R) isomer.

To a solution of 433 mg of the mixture obtained from the previous reaction in 12 mL of acetonitrile and 0.6 mL of pyridine at 0° C. was added 1.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 317 mg of material which was purified by flash chromatography to give 187 mg (69%) of N-debenzoyl-N-(4-bromobenzoyl)-3'-desphenyl-3'-(4-fluorophenyl) taxol, which was recrystallized from methanol/water.

m.p. 174.5°-175.5° C.; [α]$^{25}_{Na}$ −46.9° (c 0.00735, CHCl3).

1H NMR (CDCl3, 300 MHz) δ8.13 (d, J=7.2 Hz, 2H, benzoate ortho), 7.7–7.4 (m, 9H, aromatic), 7.10 (dd, J=8.3, 8.3 Hz, 2H, aromatic), 6.97 (d, J=8.8 Hz, 1H, NH), 6.27 (s, 1H, H10), 6.23 (dd, J=8.8, 8.8 Hz, 1H, H13), 5.76 (dd, J=8.8, 2.2 Hz, 1H, H3'), 5.67 (d, J=7.1 Hz, 1H, H2β), 4.94 (dd, J=9.9, 2.2 Hz, 1H, H5), 4.75 (dd, J=4.4, 2.2 Hz, 1H, H2'), 4.39 (m, 1H, H7), 4.31 (d, J=8.5 Hz, 1H, H20α), 4.19 (d, J=8.5 Hz, 1H, H20β), 3.79 (d, J=7.1 Hz, 1H, H3), 3.59 (d, J=4.4 Hz, 1H, 2'OH), 2.54 (m, 1H, H6α), 2.47 (d, J=4.4 Hz, 1H, 7OH), 2.36 (s, 3H, 4Ac), 2.30 (m, 2H, H14α, H14β), 2.24 (s, 3H, 10Ac), 1.88 (m, 1H, H6α), 1.78 (br s, 3H, Me18), 1.74 (s, 1H, 1OH), 1.68 (s, 3H, Me19), 1.23 (s, 3H, Me17), 1.14 (s, 3H, Me16).

EXAMPLE 20

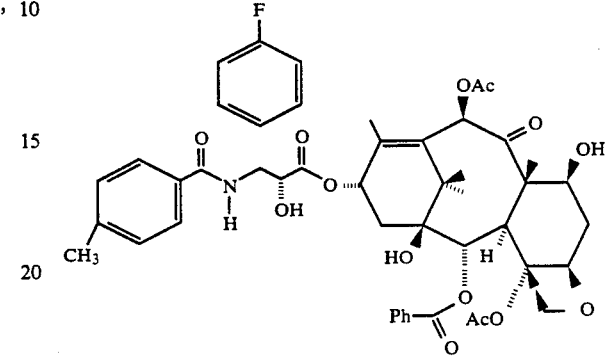

Preparation of N-debenzoyl-N-(4-methylbenzoyl)-3'-desphenyl-3'-(4-fluorophenyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-(4-methylbenzoyl)-3-triethylsilyloxy-4-(4-fluorophenyl)azetidin-2-one (592 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 335 mg of a mixture containing (2'R,3'S)-2',7-(bis)triethylsilyl-N-debenzoyl-N-(4-methylbenzoyl)-3'-desphenyl-3'-(4-fluorophenyl) taxol and a small amount of the (2'S,3'R) isomer.

To a solution of 335 mg (0.30 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 280 mg of material which was purified by flash chromatography to give 163 mg (64%) of N-debenzoyl-N-(4-methylbenzoyl)-3'-desphenyl-3'-(4-fluorophenyl) taxol, which was recrystallized from methanol/water.

m.p. 172°-173° C.; [α]$^{25}_{Na}$ −52.0° (c 0.01, CHCl3).

1H NMR (CDCl3, 300 MHz) δ8.13 (d, J=7.1 Hz, 2H, benzoate ortho), 7.61 (m, 3H, aromatic), 7.48 (m, 4H, aromatic), 7.18 (m, 2H, aromatic), 7.10 (m, 2H, aromatic), 6.95 (d, J=8.8 Hz, 1H, NH), 6.27 (s, 1H, H10), 6.21 (dd, J=8.8, 8.8 Hz, 1H, H13), 5.77 (dd, J=8.8, 2.2 Hz, 1H, H3'), 5.67 (d, J=7.2 Hz, 1H, H2β), 4.94 (dd, J=9.3, 1.7 Hz, 1H, H5), 4.75 (dd, J=4.4, 2.2 Hz, 1H, H2'), 4.39 (ddd, J=11.0, 6.6, 4.4 Hz, 1H, H7), 4.30 (d, J=8.8 Hz, 1H, H20α), 4.19 (d, J=8.8 Hz, 1H, H20β), 3.79 (d, J=7.2 Hz, 1H, H3), 3.67 (d, J=4.4 Hz, 1H, 2'OH), 2.54 (ddd, J=9.3, 14.8, 6.6 Hz, 1H, H6α), 2.46 (d, J=4.4 Hz, 1H, 7OH), 2.37 (s, 3H, 4Ac), 2.36 (s, 3H, ArMe), 2.30 (m, 2H, H14), 2.23 (s, 3H, 10Ac), 1.87 (ddd, J=11.0, 14.8, 1.7 Hz, 1H, H6β), 1.79 (br s, 3H, Me18), 1.79 (s, 1H, 1OH), 1.68 (s, 3H, Me19), 1.22 (s, 3H, Me17), 1.14 (s, 3H, Me16).

EXAMPLE 21

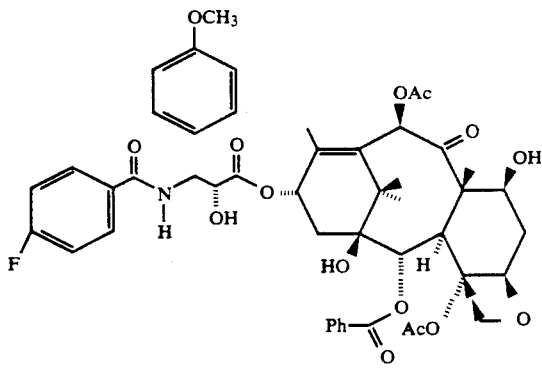

Preparation of N-debenzoyl-N-(4-fluorobenzoyl)-3'-desphenyl-3'-(4-methoxyphenyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-(4-fluorobenzoyl)-3-triethylsilyloxy-4-(4-methoxyphenyl-)azetidin-2-one (610 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 330 mg of a mixture containing (2'R,3'S)-2',7-(bis)triethylsilyl-N-debenzoyl-N-(4-fluorobenzoyl)-3'-desphenyl-3'-(4-methoxyphenyl) taxol and a small amount of the (2'S,3'R) isomer.

To a solution of 330 mg (0.292 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 260 mg of material which was purified by flash chromatography to give 155 mg (60%) of N-debenzoyl-N-(4-fluorobenzoyl)-3'-desphenyl-3'-(4-methoxyphenyl) taxol, which was recrystallized from methanol/water.

m.p. 169°–170° C.; $[\alpha]^{25}_{Na}$ −50.9° (c 0.01, CHCl3).

1H NMR (CDCl3, 300 MHz) δ8.14 (d, J=7.1 Hz, 2H, benzoate ortho), 7.57 (m, 7H, aromatic), 7.06 (m, 2H, aromatic), 6.94 (m, 2H, aromatic), 6.85 (d, J=8.8 Hz, 1H, NH), 6.27 (s, 1H, H10), 6.20 (dd, J=8.8, 8.8 Hz, 1H, H13), 5.72 (dd, J=8.8, 2.8 Hz, 1H, H3'), 5.67 (d, J=7.2 Hz, 1H, H2β), 4.94 (dd, J=9.3, 2.1 Hz, 1H, H5), 4.74 (dd, J=4.9, 2.8 Hz, 1H, H2'), 4.40 (ddd, J=11.0, 6.6, 3.9 Hz, 1H, H7), 4.31 (d, J=8.8 Hz, 1H, H20α), 4.19 (d, J=8.8 Hz, 1H, H20β), 3.80 (d, J=7.2 Hz, 1H, H3), 3.79 (s, 3H, ArOMe), 3.51 (d, J=4.9 Hz, 1H, 2'OH), 2.54 (m, 1H, H6α), 2.50 (d, J=3.9 Hz, 1H, 7OH), 2.37 (s, 3H, 4Ac), 2.31 (m, 2H, H14), 2.24 (s, 3H, 10Ac), 1.87 (m, 1H, H6β), 1.79 (br s, 3H, Me18), 1.79 (s, 1H, 1OH), 1.68 (s, 3H, Me19), 1.24 (s, 3H, Me17), 1.14 (s, 3H, Me16).

EXAMPLE 22

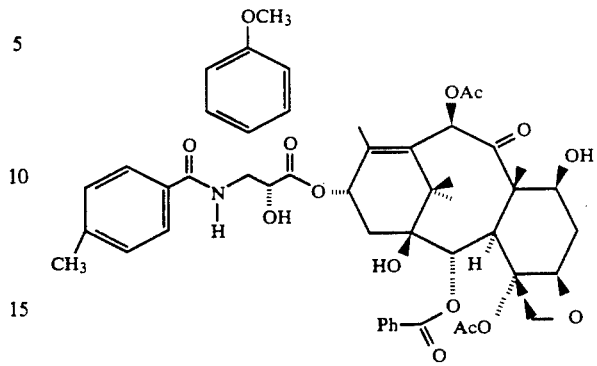

Preparation of N-debenzoyl-N-(4-methylbenzoyl)-3'-desphenyl-3'-(4-methoxyphenyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-(4-methylbenzoyl)-3-triethylsilyloxy-4-(4-methoxyphenyl-)azetidin-2-one (610 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 325 mg of a mixture containing (2'R,3'S)-2',7-(bis)triethylsilyl-N-debenzoyl-N-(4-methylbenzoyl)-3'-desphenyl-3'-(4-methoxyphenyl) taxol and a small amount of the (2'S,3'R) isomer.

To a solution of 325 mg (0.289 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 265 mg of material which was purified by flash chromatography to give 165 mg (64%) of N-debenzoyl-N-(4-methylbenzoyl)-3'-desphenyl-3'-(4-methoxyphenyl) taxol, which was recrystallized from methanol/water.

m.p. 173°–174° C.; $[\alpha]^{25}_{Na}$ −50.2° (c 0.01, CHCl3).

1H NMR (CDCl3, 300 MHz) δ8.13 (d, J=7.1 Hz, 2H, benzoate ortho), 7.61 (m, 3H, aromatic), 7.51 (m, 2H, aromatic), 7.40 (m, 2H, aromatic), 7.19 (m, 2H, aromatic), 6.93 (m, 2H, aromatic), 6.86 (d, J=8.8 Hz, 1H, NH), 6.27 (s, 1H, H10), 6.21 (dd, J=8.8, 8.8 Hz, 1H, H13), 5.70 (dd, J=8.8, 2.8 Hz, 1H, H3'), 5.66 (d, J=7.2 Hz, 1H, H2β), 4.94 (dd, J=9.9, 2.2 Hz, 1H, H5), 4.74 (dd, J=5.5, 2.8 Hz, 1H, H2'), 4.40 (ddd, J=11.0, 6.5, 3.8 Hz, 1H, H7), 4.30 (d, J=8.8 Hz, 1H, H20α), 4.19 (d, J=8.8 Hz, 1H, H20β), 3.79 (d, J=7.2 Hz, 1H, H3), 3.78 (s, 3H, ArOMe), 3.63 (d, J=5.5 Hz, 1H, 2'OH), 2.54 (m, 1H, H6α), 2.46 (d, J=3.8 Hz, 1H, 7OH), 2.38 (s, 3H, ArMe), 2.37 (s, 3H, 4Ac), 2.31 (m, 2H, H14), 2.23 (s, 3H, 10Ac), 1.88 (m, 1H, H6β), 1.80 (br s, 3H, Me18), 1.80 (s, 1H, 1OH), 1.68 (s, 3H, Me19), 1.23 (s, 3H, Me17), 1.14 (s, 3H, Me16).

EXAMPLE 23

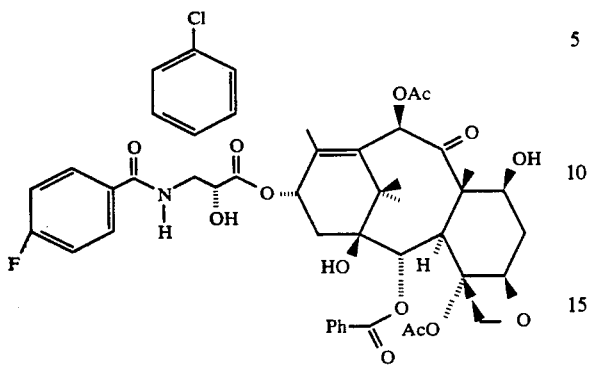

Preparation of N-debenzoyl-N-(4-fluorobenzoyl)-3'-desphenyl-3'-(4-chlorophenyl) taxol.

To a solution of 7-triethylsilyl baccatin III (200 mg, 0.286 mmol)) in 2 mL of THF at −45° C. was added dropwise 0.174 mL of a 1.63M solution of nBuLi in hexane. After 0.5 h at −45° C., a solution of cis-1-(4-fluorobenzoyl)-3-triethylsilyloxy-4-(4-chlorophenyl-)azetidin-2-one (620 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 325 mg of a mixture containing (2'R,3'S)-2',7-(bis)triethylsilyl-N-debenzoyl-N-(4-fluorobenzoyl)-3'-desphenyl-3'-(4-chlorophenyl) taxol and a small amount of the (2'S,3'R) isomer.

To a solution of 325 mg (0.286 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 260 mg of material which was purified by flash chromatography to give 161 mg (62%) of N-debenzoyl-N-(4-fluorobenzoyl)-3'-desphenyl-3'-(4-chlorophenyl) taxol, which was recrystallized from methanol/water.

m.p. 172°-174° C.; $[\alpha]^{25}_{Na}$ −56.0° (c 0.01, CHCl$_3$).

$^1$H NMR (CDCl$_3$, 300 MHz) δ8.12 (d, J=7.1 Hz, 2H, benzoate ortho), 7.73 (m, 2H, aromatic), 7.60 (m, 1H, aromatic), 7.50 (m, 2H, aromatic), 7.38 (m, 4H, aromatic), 7.06 (m, 2H, aromatic), 7.05 (d, J=8.8 Hz, 1H, NH), 6.27 (s, 1H, H10), 6.22 (dd, J=7.7, 7.7 Hz, 1H, H13), 5.75 (dd, J=8.8, 2.8 Hz, 1H, H3'), 5.65 (d, J=7.1 Hz, 1H, H2β), 4.92 (dd, J=9.3, 1.6 Hz, 1H, H5), 4.75 (dd, J=4.9, 2.8 Hz, 1H, H2'), 4.41 (m, 1H, H7), 4.29 (d, J=8.2 Hz, 1H, H20α), 4.17 (d, J=8.2 Hz, 1H, H20β), 3.84 (d, J=4.4 Hz, 1H, 2'OH), 3.78 (d, J=7.1 Hz, 1H, H3), 2.55 (d, J=4.4 Hz, 1H, 7OH), 2.52 (m, 1H, H6α), 2.36 (s, 3H, 4Ac), 2.29 (m, 2H, H14), 2.21 (s, 3H, 10Ac), 1.86 (m, 1H, H6β), 1.79 (br s, 3H, Me18), 1.78 (s, 1H, 1OH), 1.67 (s, 3H, Me19), 1.24 (s, 3H, Me17), 1.12 (s, 3H, Me16).

EXAMPLE 24

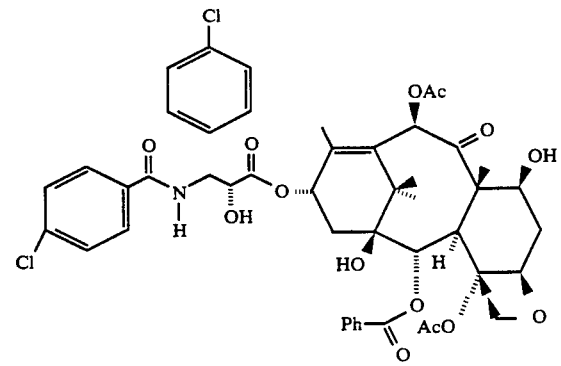

Preparation of N-debenzoyl-N-(4-chlorobenzoyl)-3'-desphenyl-3'-(4-chlorophenyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-(4-chlorobenzoyl)-3-triethylsilyloxy-4-(4-chlorophenyl-)azetidin-2-one (640 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 335 mg of a mixture containing (2'R,3'S)-2',7-(bis)triethylsilyl-N-debenzoyl-N-(4-chloroobenzoyl)-3'-desphenyl-3'-(4-chlorophenyl) taxol and a small amount of the (2'S,3'R) isomer.

To a solution of 335 mg (0.291 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 270 mg of material which was purified by flash chromatography to give 158 mg (60%) of N-debenzoyl-N-(4-chlorobenzoyl)-3'-desphenyl-3'-(4-chlorophenyl) taxol, which was recrystallized from methanol/water.

m.p. 184°-185° C.; $[\alpha]^{25}_{Na}$ −52.5° (c 0.01, CHCl$_3$).

$^1$H NMR (CDCl$_3$, 300 MHz) δ8.13 (d, J=7.1 Hz, 2H, benzoate ortho), 7.51 (m, 11H, aromatic), 6.98 (d, J=8.8 Hz, 1H, NH), 6.27 (s, 1H, H10), 6.22 (dd, J=8.8, 8.8 Hz, 1H, H13), 5.76 (dd, J=8.8, 2.2 Hz, 1H, H3'), 5.67 (d, J=7.2 Hz, 1H, H2β), 4.94 (dd, J=9.9, 2.2 Hz, 1H, H5), 4.76 (dd, J=5.0, 2.2 Hz, 1H, H2'), 4.39 (ddd, J=10.8, 6.5, 4.4 Hz, 1H, H7), 4.30 (d, J=8.8 Hz, 1H, H20α), 4.19 (d, J=8.8 Hz, 1H, H20β), 3.79 (d, J=7.2 Hz, 1H, H3), 3.68 (d, J=5.0 Hz, 1H, 2'OH), 2.54 (ddd, J=9.9, 14.8 6.5 Hz, 1H, H6α), 2.47 (d, J=4.4 Hz, 1H, 7OH), 2.37 (s, 3H, 4Ac), 2.30 (m, 2H, H14), 2.23 (s, 3H, 10Ac), 1.87 (ddd, J=10.8, 14.8 2.2 Hz, 1H, H6β), 1.84 (br s, 3H, Me18), 1.79 (s, 1H, 1OH), 1.68 (s, 3H, Me19), 1.22 (s, 3H, Me17), 1.14 (s, 3H, Me16).

EXAMPLE 25

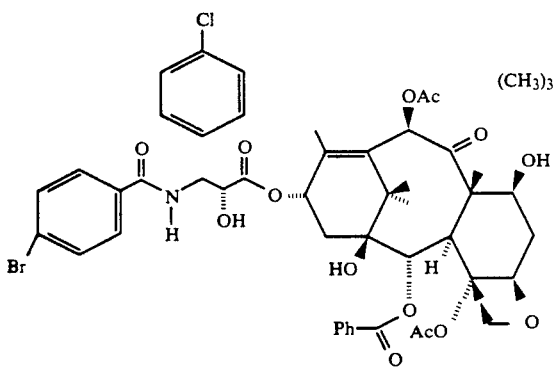

Preparation of N-debenzoyl-N-(4-bromobenzoyl)-3'-desphenyl-3'-(4-chlorophenyl) taxol.

To a solution of 7-triethylsilyl baccatin III (200 mg, 0.285 mmol) in 2 mL of THF at −45° C. was added dropwise 0.175 mL of a 1.63M solution of nBuLi in hexane. After 0.5 h at −45° C., a solution of cis-1-(4-bromobenzoyl)-3-triethylsilyloxy-4-(4-chlorophenyl)azetidin-2-one (354 mg, 0.715 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 355 mg of a mixture containing (2'R,3'S)-2',7-(bis)triethylsilyl-N-debenzoyl-N-(4-bromobenzoyl)-3'-desphenyl-3'-(4-chlorophenyl) taxol and a small amount of the (2'S,3'R) isomer.

To a solution of 355 mg of the mixture obtained from the previous reaction in 12 mL of acetonitrile and 0.6 mL of pyridine at 0° C. was added 1.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 280 mg of material which was purified by flash chromatography to give 171 mg (62%) of N-debenzoyl-N-(4-bromobenzoyl)-3'-desphenyl-3'-(4-chlorophenyl) taxol, which was recrystallized from methanol/water.

m.p. 181°–183.5° C.; $[\alpha]^{25}_{Na}$ −52.8° (c 0.0064, CHCl3).

$^1$H NMR (CDCl3, 300 MHz) δ8.12 (d, J=7.2 Hz, 2H, benzoate ortho), 7.65-7.3 (m, 11H, aromatic), 7.03 (d, J=8.8 Hz, 1H, NH), 6.27 (s, 1H, H10), 6.22 (dd, J=9.3, 9.3 Hz, 1H, H13), 5.75 (dd, J=8.8, 2.2 Hz, 1H, H3'), 5.66 (d, J=7.1 Hz, 1H, H2β), 4.93 (dd, J=9.9, 2.2 Hz, 1H, H5), 4.75 (dd, J=5.0, 2.2 Hz, 1H, H2'), 4.40 (m, 1H, H7), 4.30 (d, J=8.5 Hz, 1H, H20α), 4.18 (d, J=8.5 Hz, 1H, H20β), 3.77 (m, 2H, H3, 2'OH), 2.54 (m, 1H, H6α), 2.52 (d, J=4.4 Hz, 1H, 7OH), 2.36 (s, 3H, 4Ac), 2.29 (m, 2H, H14α, H14β), 2.22 (s, 3H, 10Ac), 1.87 (m, 1H, H6α), 1.79 (br s, 3H, Me18), 1.73 (s, 1H, 1OH), 1.67 (s, 3H, Me19), 1.21 (s, 3H, Me17), 1.13 (s, 3H, Me16).

EXAMPLE 26

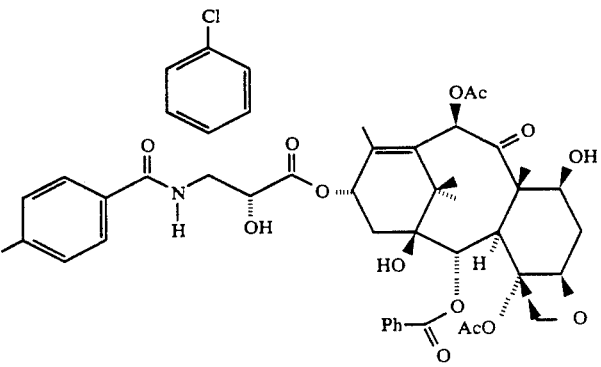

Preparation of N-debenzoyl-N-(4-t-butylbenzoyl)-3'-desphenyl-3'-(4-chlorophenyl) taxol.

To a solution of 7-triethylsilyl baccatin III (200 mg, 0.285 mmol) in 2 mL of THF at −45° C. was added dropwise 0.175 mL of a 1.63M solution of nBuLi in hexane. After 0.5 h at −45° C., a solution of cis-1-(4-t-butylbenzoyl)-3-triethylsilyloxy-4-(4-chlorophenyl)azetidin-2-one (675 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 317 mg of a mixture containing (2'R,3'S)-2',7-(bis)triethylsilyl-N-debenzoyl-N-(4-t-butylbenzoyl)-3'-desphenyl-3'-(4-chlorophenyl) taxol and a small amount of the (2'S,3'R) isomer.

To a solution of 317 mg of the mixture obtained from the previous reaction in 12 mL of acetonitrile and 0.6 mL of pyridine at 0° C. was added 1.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 354 mg of material which was purified by flash chromatography to give 186 mg (69%) of N-debenzoyl-N-(4-t-butylbenzoyl)-3'-desphenyl-3'-(4-chlorophenyl) taxol, which was recrystallized from methanol/water.

m.p. 176.5°–178° C.; $[\alpha]^{25}_{Na}$ −51.8° (c 0.00985, CHCl3).

$^1$H NMR (CDCl3, 300 MHz) δ8.14 (d, J=8.8 Hz, 2H, benzoate ortho), 7.7-7.3 (m, 11H, aromatic), 6.94 (d, J=8.8 Hz, 1H, NH), 6.27 (s, 1H, H10), 6.24 (dd, J=8.3, 8.3 Hz, 1H, H13), 5.78 (dd, J=9.3, 2.2 Hz, 1H, H3'), 5.67 (d, J=7.1 Hz, 1H, H2β), 4.95 (dd, J=8.8, 1.1 Hz, 1H, H5), 4.76 (dd, J=5.0, 2.2 Hz, 1H, H2'), 4.40 (m, 1H, H7), 4.31 (d, J=8.5 Hz, 1H, H20α), 4.20 (d, J=8.5 Hz, 1H, H20β), 3.80 (d, J=7.1 Hz, 1H, H3), 3.64 (d, J=5.0

Hz, 1H, 2'OH), 2.55 (m, 1H, H6α), 2.46 (d, J=4.4 Hz, 1H, 7OH), 2.38 (s, 3H, 4Ac), 2.32 (m, 2H, H14α, H14β), 2.23 (s, 3H, 10Ac), 1.88 (m, 1H, H6α), 1.82 (br s, 3H, Me18), 1.77 (s, 1H, 1OH), 1.67 (s, 3H, Me19), 1.30 (s, 9H, tBu), 1.23 (s, 3H, Me17), 1.14 (s, 3H, Me16).

EXAMPLE 27

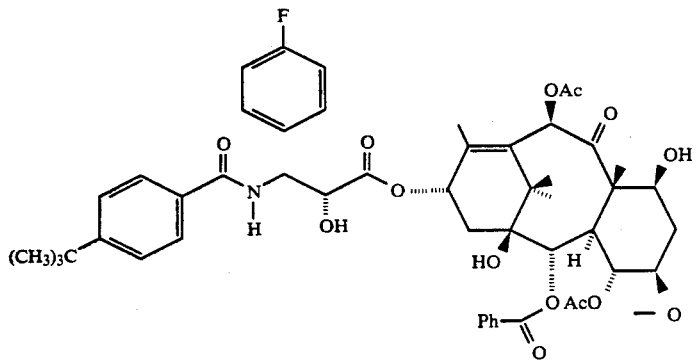

Preparation of N-debenzoyl-N-(4-t-butylbenzoyl)-3'-desphenyl-3'-(4-fluorophenyl) taxol.

To a solution of 7-triethylsilyl baccatin III (200 mg, 0.286 mmol)) in 2 mL of THF at −45° C. was added dropwise 0.174 mL of a 1.63M solution of nBuLi in hexane. After 0.5 h at −45° C., a solution of cis-1-(4-t-butylbenzoyl)-3-triethylsilyloxy-4-(4-fluorophenyl-)azetidin-2-one (650 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 330 mg of a mixture containing (2'R,3'S)-2',7-(bis)triethylsilyl-N-debenzoyl-N-(4-t-butylbenzoyl)-3'-desphenyl-3'-(4-fluorophenyl) taxol and a small amount of the (2'S,3'R) isomer.

To a solution of 330 mg (0.286 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 260 mg of material which was purified by flash chromatography to give 168 mg (64%) of N-debenzoyl-N-(4-t-butylbenzoyl)-3'-desphenyl-3'-(4-fluorophenyl) taxol, which was recrystallized from methanol/water.

m.p. 180°–182° C.; [α]$^{25}_{Na}$ −46.3° (c 0.01, CHCl3).

1H NMR (CDCl3, 300 MHz) δ8.12 (d, J=7.1 Hz, 2H, benzoate ortho), 7.67 (m, 2H, aromatic), 7.60 (m, 1H, aromatic), 7.46 (m, 6H, aromatic), 7.08 (m, 2H, aromatic), 7.00 (d, J=8.8 Hz, 1H, NH), 6.27 (s, 1H, H10), 6.23 (dd, J=8.8, 8.8 Hz, 1H, H13), 5.76 (dd, J=8.8, 2.7 Hz, 1H, H3'), 5.67 (d, J=7.1 Hz, 1H, H2β), 4.94 (dd, J=9.3, 1.7 Hz, 1H, H5), 4.75 (dd, J=4.9, 2.7 Hz, 1H, H2'), 4.39 (m, 1H, H7), 4.30 (d, J=8.2 Hz, 1H, H20α), 4.22 (d, J=8.2 Hz, 1H, H20β), 3.78 (d, J=7.1 Hz, 1H, H3), 3.55 (d, J=4.9 Hz, 1H, 2'OH), 2.56 (m, 1H, H6α), 2.50 (d, J=4.4 Hz, 1H, 7OH), 2.37 (s, 3H, 4Ac), 2.30 (m, 2H, H14), 2.22 (s, 3H, 10Ac), 1.88 (m, 1H, H6β), 1.79 (br s, 3H, Me18), 1.75 (s, 1H, 1OH), 1.67 (s, 3H, Me19), 1.29 (s, 9H, Ar'Bu), 1.22 (s, 3H, Me17), 1.13 (s, 3H, Me16).

EXAMPLE 28

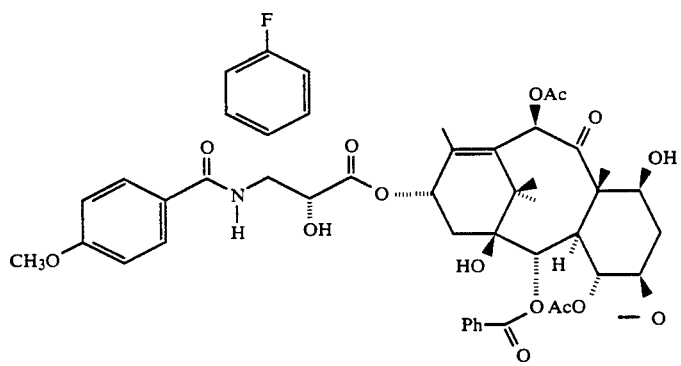

Preparation of N-debenzoyl-N-(4-methoxybenzoyl)-3'-desphenyl-3'-(4-fluorophenyl) taxol.

To a solution of 7-triethylsilyl baccatin III (200 mg, 0.285 mmol) in 2 mL of THF at −45° C. was added dropwise 0.175 mL of a 1.63M solution of nBuLi in hexane. After 0.5 h at −45° C., a solution of cis-1-(4-methoxybenzoyl)-3-triethylsilyloxy-4-(4-fluorophenyl-)azetidin-2-one (614 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO3 and 60/40 ethyl acetate/hexane. Evaporation of the organic layer gave a residue which was purified by filtration through silica gel to give 362 mg of a mixture containing (2'R,3'S)-2',7-(bis)triethylsilyl-N-debenzoyl-N-(4-methoxybenzoyl)-3'-desphenyl-3'-(4-fluorophenyl) taxol and a small amount of the (2'S,3'R) isomer.

To a solution of 362 mg of the mixture obtained from the previous reaction in 12 mL of acetonitrile and 0.6 mL of pyridine at 0° C. was added 1.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 269 mg of material which was purified by flash chromatography to give 183 mg (71%) of N-debenzoyl-N-(4-methoxybenzoyl)-3'-desphenyl-3'-(4-fluorophenyl) taxol, which was recrystallized from methanol/water.

m.p. 172.5°-174.5° C.; $[\alpha]^{25}_{Na}$ −47.0° (c 0.0044, CHCl$_3$).

$^1$H NMR (CDCl$_3$, 300 MHz) δ8.13 (d, J=7.2 Hz, 2H, benzoate ortho), 7.7–7.4 (m, 9H, aromatic), 7.10 (dd, J=8.8, 8.8 Hz, 2H, aromatic), 6.97 (d, J=8.8 Hz, 1H, NH), 6.27 (s, 1H, H10), 6.23 (dd, J=8.8, 8.8 Hz, 1H, H13), 5.76 (dd, J=8.8, 2.2 Hz, 1H, H3'), 5.67 (d, J=7.1 Hz, 1H, H2β), 4.94 (dd, J=9.9, 2.2 Hz, 1H, H5), 4.75 (dd, J=4.4, 2.2 Hz, 1H, H2'), 4.39 (m, 1H, H7), 4.31 (d, J=8.5 Hz, 1H, H20α), 4.19 (d, J=8.5 Hz, 1H, H20β), 3.79 (d, J=7.1 Hz, 1H, H3), 3.59 (d, J=4.4 Hz, 1H, 2'OH), 2.54 (m, 1H, H6α), 2.47 (d, J=4.4 Hz, 1H, 7OH), 2.36 (s, 3H, 4Ac), 2.30 (m, 2H, H14α, H14β), 2.24 (s, 3H, 10Ac), 1.88 (m, 1H, H6α), 1.78 (br s, 3H, Me18), 1.74 (s, 1H, 1OH), 1.68 (s, 3H, Me19), 1.23 (s, 3H, Me17), 1.14 (s, 3H, Me16).

EXAMPLE 29

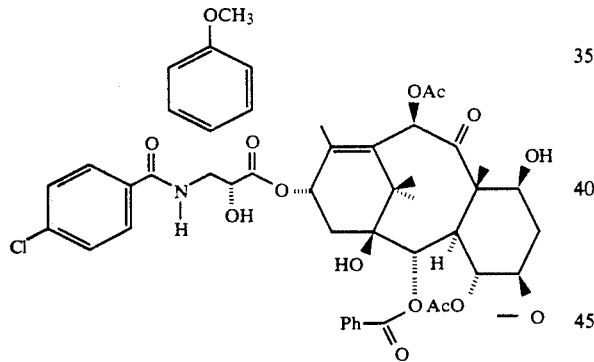

Preparation of N-debenzoyl-N-(4-chlorobenzoyl)-3'-desphenyl-3'-(4-methoxyphenyl) taxol.

To a solution of 7-triethylsilyl baccatin III (200 mg, 0.286 mmol)) in 2 mL of THF at −45° C. was added dropwise 0.174 mL of a 1.63M solution of nBuLi in hexane. After 0.5 h at −45° C., a solution of cis-1-(4-chlorobenzoyl)-3-triethylsilyloxy-4-(4-methoxyphenyl)azetidin-2-one (638 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 328 mg of a mixture containing (2'R,3'S)-2',7-(bis)triethylsilyl-N-debenzoyl-N-(4-chlorobenzoyl)-3'-desphenyl-3'-(4-methoxyphenyl) taxol and a small amount of the (2'S,3'R) isomer.

To a solution of 328 mg (0.286 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 270 mg of material which was purified by flash chromatography to give 170 mg (65%) of N-debenzoyl-N-(4-chlorobenzoyl)-3'-desphenyl-3'-(4-methoxyphenyl) taxol, which was recrystallized from methanol/water.

m.p. 169°–171° C.; $[\alpha]^{25}_{Na}$ −51.1° (c 0.035, CHCl$_3$).

$^1$H NMR (CDCl$_3$, 300 MHz) δ8.12 (d, J=7.1 Hz, 2H, benzoate ortho), 7.65 (d, J=8.2 Hz, 2H, benzamide ortho), 7.51 (m, 2H, aromatic), 7.36 (m, 5H, aromatic), 6.91 (m, 2H, aromatic), 6.90 (d, J=8.2 Hz, 1H, NH), 6.26 (s, 1H, H10), 6.21 (dd, J=7.7, 8.9 Hz, 1H, H13), 5.69 (dd, J=8.2, 2.8 Hz, 1H, H3'), 5.67 (d, J=6.6 Hz, 1H, H2β), 4.94 (dd, J=9.9, 2.2 Hz, 1H, H5), 4.74 (dd, J=4.9, 2.8 Hz, 1H, H2'), 4.39 (ddd, J=11.0, 6.6, 3.8 Hz, 1H, H7), 4.30 (d, J=8.2 Hz, 1H, H20α), 4.19 (d, J=8.2 Hz, 1H, H20β), 3.79 (d, J=6.6 Hz, 1H, H3), 3.79 (s, 3H, ArOMe), 3.57 (d, J=4.9 Hz, 1H, 2'OH), 2.53 (ddd, J=9.9, 14.4, 6.6 Hz, 1H, H6α), 2.47 (d, J=3.8 Hz, 1H, 7OH), 2.36 (s, 3H, 4Ac), 2.33 (m, 2H, H14), 2.23 (s, 3H, 10Ac), 1.88 (ddd, J=11.0, 14.4, 2.2 Hz, 1H, H6β), 1.79 (br s, 3H, Me18), 1.78 (s, 1H, 1OH), 1.68 (s, 3H, Me19), 1.23 (s, 3H, Me17), 1.14 (s, 3H, Me16).

EXAMPLE 30

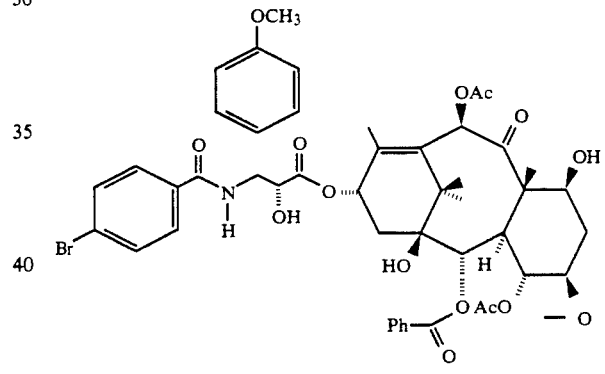

Preparation of N-debenzoyl-N-(4-bromobenzoyl)-3'-desphenyl-3'-(4-methoxyphenyl) taxol.

To a solution of 7-triethylsilyl baccatin III (200 mg, 0.285 mmol) in 2 mL of THF at −45° C. was added dropwose 0.175 mL of a 1.63M solution of nBuLi in hexane. After 0.5 h at −45° C., a solution of cis-1-(4-bromobenzoyl)-3-triethylsilyloxy-4-(4-methoxyphenyl)azetidin-2-one (696 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 321 mg of a mixture containing (2'R,3'S)-2',7-(bis)triethylsilyl-N-debenzoyl-N-(4-bromobenzoyl)-3'-(4-methoxyphenyl) taxol and a small amount of the (2'S,3'R) isomer.

To a solution of 351 mg of the mixture obtained from the previous reaction in 12 mL of acetonitrile and 0.6 mL of pyridine at 0° C. was added 1.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 320 mg of material which was purified by flash chromatography to give 189 mg (69%) of N-debenzoyl-N-(4-bromobenzoyl)-3'-desphenyl-3'-(4-methoxyphenyl) taxol, which was recrystallized from methanol/water.

m.p. 173.5°–176° C.; $[\alpha]^{25}_{Na}$ −48.9° (c 0.0065, CHCl₃).

¹H NMR (CDCl₃, 300 MHz) δ8.13 (d, J=7.2 Hz, 2H, benzoate ortho), 7.7–7.3 (m, 9H, aromatic), 6.93 (d, J=8.8, Hz, 2H, aromatic), 6.93 (d, J=9.3 Hz, 1H, NH), 6.27 (s, 1H, H10), 6.21 (dd, J=8.8, 8.8 Hz, 1H, H13), 5.68 (m, 2H, H3', H2β), 4.94 (dd, J=8.8, 1.7 Hz, 1H, H5), 4.74 (dd, J=4.9, 2.8 Hz, 1H, H2'), 4.40 (m, 1H, H7), 4.31 (d, J=8.2 Hz, 1H, H20α), 4.19 (d, J=8.2 Hz, 1H, H20β), 3.80 (d, J=7.1 Hz, 1H, H3), 3.80 (s, 3H, ArOMe), 3.51 (d, J=4.9 Hz, 1H, 2'OH), 2.54 (m, 1H, H6α), 2.46 (d, J=4.4 Hz, 1H, 7OH), 2.37 (s, 3H, 4Ac), 2.31 (m, 2H, H14α, H14β), 2.24 (s, 3H, 10Ac), 1.87 (m, 1H, H6α), 1.79 (br s, 3H, Me18), 1.74 (s, 1H, 1OH), 1.68 (s, 3H, Me19), 1.23 (s, 3H, Me17), 1.14 (s, 3H, Me16).

EXAMPLE 31

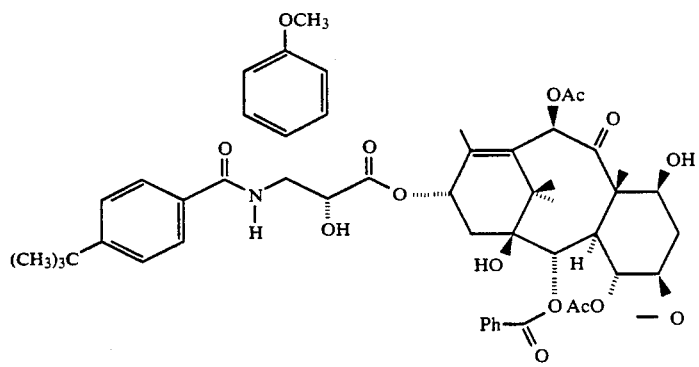

Preparation of N-debenzoyl-N-(4-t-butylbenzoyl)-3'-desphenyl-3'-(4-methoxyphenyl) taxol.

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-(4-t-butylbenzoyl)-3-triethylsilyloxy-4-(4-methoxyphenyl-)azetidin-2-one (670 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 340 mg of a mixture containing (2'R,3'S)-2',7-(bis)triethylsilyl-N-debenzoyl-N-(4-t-butylbenzoyl)-3'-desphenyl-3'-(4-methoxyphenyl) taxol and a small amount of the (2'S,3'R) isomer.

To a solution of 340 mg (0.291 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 275 mg of material which was purified by flash chromatography to give 188 mg (70%) of N-debenzoyl-N-(4-t-butylbenzoyl)-3'-desphenyl-3'-(4-methoxyphenyl) taxol, which was recrystallized from methanol/water.

m.p. 184°–185° C.; $[\alpha]^{25}_{Na}$ −50.4° (c 0.01, CHCl₃).

¹H NMR (CDCl₃, 300 MHz) δ8.13 (d, J=7.1 Hz, 2H, benzoate ortho), 7.53 (m, 9H, aromatic), 6.92 (m, 2H, aromatic), 6.88 (d, J=8.8 Hz, 1H, NH), 6.27 (s, 1H, H10), 6.21 (dd, J=8.8, 8.8 Hz, 1H, H13), 5.72 (dd, J=8.8, 2.8 Hz, 1H, H3'), 5.67 (d, J=7.1 Hz, 1H, H2β), 4.95 (dd, J=9.8, 2.2 Hz, 1H, H5), 4.74 (dd, J=5.5, 2.8 Hz, 1H, H2'), 4.40 (ddd, J=11.0, 6.6, 3.8 Hz, 1H, H7), 4.30 (d, J=8.4 Hz, 1H, H20α), 4.19 (d, J=8.4 Hz, 1H, H20β), 3.80 (d, J=7.1 Hz, 1H, H3), 3.79 (s, 3H, ArOMe), 3.63 (d, J=5.5 Hz, 1H, 2'OH), 2.54 (m, 1H, H6α), 2.46 (d, J=3.8 Hz, 1H, 7OH), 2.38 (s, 3H, 4Ac), 2.32 (m, 2H, H14), 2.23 (s, 3H, 10Ac), 1.87 (ddd, J=11.0, 14.7, 2.2 Hz, 1H, H6β), 1.81 (br s, 3H, Me18), 1.80 (s, 1H, 1OH), 1.68 (s, 3H, Me19), 1.30 (s, 9H, Ar'Bu), 1.23 (s, 3H, Me17), 1.14 (s, 3H, Me16).

EXAMPLE 32

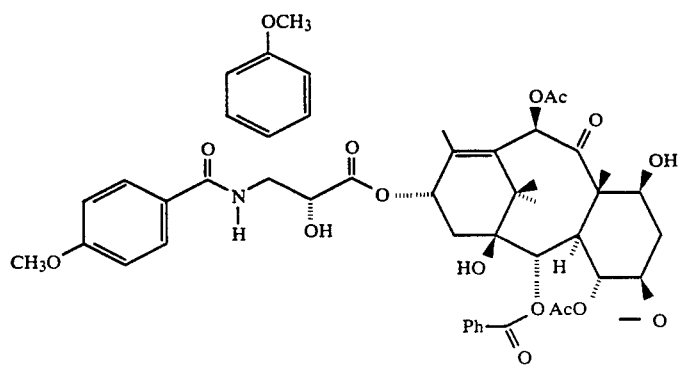

Preparation of N-debenzoyl-N-(4-methoxybenzoyl)-3'-desphenyl-3'-(4-methoxyphenyl) taxol.

To a solution of 7-triethylsilyl baccatin III (200 mg, 0.286 mmol)) in 2 mL of THF at −45° C. was added dropwise 0.174 mL of a 1.63M solution of nBuLi in hexane. After 0.5 h at −45° C., a solution of cis-1-(4-methoxybenzoyl)-3-triethylsilyloxy-4-(4-methoxyphenyl)azetidin-2-one (630 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 330 mg of a mixture containing (2'R,3'S)-2',7-(bis)triethylsilyl-N-debenzoyl-N-(4-methoxybenzoyl)-3'-desphenyl-3'-(4-methoxyphenyl) taxol and a small amount of the (2'S,3'R) isomer.

To a solution of 330 mg (0.289 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 255 mg of material which was purified by flash chromatography to give 183 mg (70%) of N-debenzoyl-N-(4-methoxybenzoyl)-3'-desphenyl-3'-(4-methoxyphenyl) taxol, which was recrystallized from methanol/water. m.p. 174°-175° C.; $[\alpha]^{25}_{Na}$ −50.6° (c 0.01, CHCl$_3$).

$^1$H NMR (CDCl$_3$, 300 MHz) δ8.13 (d, J=7.1 Hz, 2H, benzoate ortho), 7.69 (d, J=8.8 Hz, 2H, benzamide ortho), 7.62 (m, 1H, aromatic), 7.51 (m, 2H, aromatic), 7.39 (m, 2H, aromatic), 6.90 (m, 4H, aromatic), 6.82 (d, J=8.2 Hz, 1H, NH), 6.27 (s, 1H, H10), 6.20 (dd, J=8.8, 8.8 Hz, 1H, H13); 5.69 (dd, J=8.2, 2.7 Hz, 1H, H3'), 5.67 (d, J=6.6 Hz, 1H, H2β), 4.95 (dd, J=7.7, 1.6 Hz, 1H, H5), 4.73 (dd, J=5.5, 2.7 Hz, 1H, H2'), 4.40 (ddd, J=11.0, 6.6, 4.4 Hz, 1H, H7), 4.30 (d, J=8.24 Hz, 1H, H20α), 4.19 (d, J=8.24 Hz, 1H, H20β), 3.81 (s, 3H, ArOMe), 3.80 (d, J=6.6 Hz, 1H, H3), 3.78 (s, 3H, ArOMe), 3.71 (d, J=5.5 Hz, 1H, 2'OH), 2.54 (ddd, J=7.7, 14.3, 6.6 Hz, 1H, H6α), 2.47 (d, J=4.4 Hz, 1H, 7OH), 2.37 (s, 3H, 4Ac), 2.31 (m, 2H, H14), 2.23 (s, 3H, 10Ac), 1.89 (ddd, J=11.0, 14.3, 1.6 Hz, 1H, H6β), 1.79 (br s, 3H, Me18), 1.69 (s, 1H, 1OH), 1.67 (s, 3H, Me19), 1.23 (s, 3H, Me17), 1.13 (s, 3H, Me16).

EXAMPLE 33

Tubulin binding assays were performed using compounds from the previous Examples substantially as set forth in Parness et al., *J. Cell Biology* 91: 479-487 (1981) and compared to taxol and taxotere. The results are presented in Table 1.

TABLE 1

| Compound | Tubulin Assay | |
|---|---|---|
| | Init. Peak | Rel. Rate |
| Example | | |
| 1 | 0 | 0 |
| 2 | 0 | 0 |
| 3 | 59 | 87 |
| 4 | 94 | 97 |
| 5 | 5 | 74 |
| 6 | 53 | 85 |
| 7 | 11 | 26 |
| 8 | 114 | 105 |

TABLE 1-continued

| Compound | Tubulin Assay | |
|---|---|---|
| | Init. Peak | Rel. Rate |
| 9 | 100 | |
| 10 | 75 | 90 |
| 11 | 67 | 88 |
| 12 | 107 | 110 |
| 13 | 67 | 85 |
| 14 | 95 | 99 |
| 15 | 89 | 98 |
| 16 | 66 | 90 |
| 17 | 101 | 98 |
| 18 | 109 | 92 |
| 19 | 88 | 100 |
| 20 | 85 | 98 |
| 21 | 45 | 81 |
| 22 | 77 | 96 |
| 23 | 63 | 88 |
| 24 | 35 | 60 |
| 25 | 60 | 83 |
| 26 | 13 | 23 |
| 27 | 55 | 82 |
| 28 | 106 | 97 |
| 29 | 42 | 72 |
| 30 | 44 | 70 |
| 31 | 24 | 44 |
| 32 | 51 | 81 |
| Taxol | 100 | 98 |
| Taxotere | 100 | — |

EXAMPLE 34

IC$_{50}$ data were obtained in vitro on a human cancer cell line (HCT 116) which is available from the National Cancer Institute, and a multidrug resistant cell line (HCT/VM46), which is resistant to a variety of hydrophobic agents, including taxol. Cytotoxicity was assessed in HCT116 and HCT VM46 human colon carcinoma cells by XTT (2,3-bis(2-methoxy-4-nitro-5-sulfophenyl)-5-[(phenylamino)carbonyl]-2H-tetrazolium hydroxide assay (Scudiero et al, "Evaluation of a soluble tetrazolium/formazan assay for cell growth and drug sensitivity in culture using human and other tumor cell line", Cancer Res. 48:4827-4833, 1988). Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance the greater the number of live cells. The results are expressed as an IC$_{50}$ which is the drug concentration required to inhibit cell proliferation (i.e. absorbance at 450 nm) to 50% of that of untreated control cells. The results are presented in Table 2. Lower numbers indicate greater activity.

TABLE 2

| Compound | IC$_{50}$ | |
|---|---|---|
| | HCT 116 | HCT VM46 |
| Example | | |
| 1 | .385 | 2.58 |
| 2 | .084 | 1.89 |
| 3 | .005 | 0.469 |
| 4 | .018 | 0.825 |
| 5 | .025 | 1.38 |
| 6 | .021 | 1.7 |
| 7 | .303 | >7.8 |
| 8 | .014 | 2.6 |
| 9 | .014 | 0.817 |
| 10 | .009 | 2.26 |

TABLE 2-continued

| Compound | IC$_{50}$ HCT 116 | HCT VM46 |
|---|---|---|
| 11 | .014 | 1.85 |
| 12 | .005 | 0.442 |
| 13 | .006 | 0.651 |
| 14 | .004 | 0.973 |
| 15 | .005 | 2.17 |
| Taxol | 0.004 | 0.536 |
| Taxotere | 0.007 | 0.246 |

In view of the above, it will be seen that the several objects of the invention are achieved.

As various changes could be made in the above compositions without departing from the scope of the invention, it is intended that all matter contained in the above description be interpreted as illustrative and not in a limiting sense.

What I claim is:

1. A taxane derivative of the formula

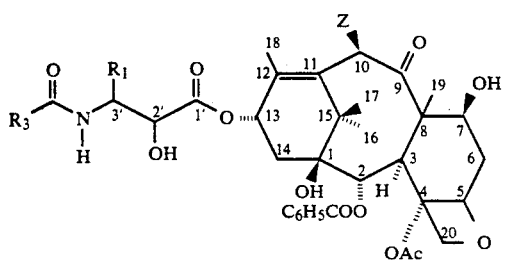

wherein

R$_1$ and R$_3$ are independently selected from the group comprising phenyl, naphthyl, C$_6$H$_5$CHCH—, and

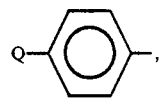

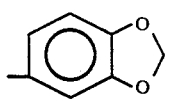

or

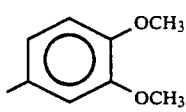

provided, however, R$_1$ and R$_3$ are not both phenyl;

Q is CH$_3$—, (CH$_3$)$_3$C—, Cl, Br, F, or NO$_2$,

Z is —OT$_1$,

T$_1$ is hydrogen, hydroxyl protecting group, or —COT$_2$,

T$_2$ is H, C$_1$-C$_6$ alkyl, C$_2$-C$_6$ alkenyl, C$_2$-C$_6$ alkynyl or monocylic aryl, and Ac is acetyl.

2. The taxane derivative of claim 1 wherein R$_1$ is

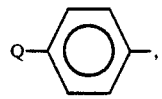

and Q is as defined in claim 1.

3. The taxane derivative of claim 2 wherein R$_3$ is phenyl or

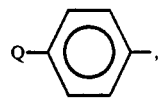

and Q is as defined in claim 1.

4. The taxane derivative of claim 1 wherein R$_3$ is

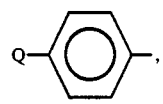

and Q is as defined in claim 1.

5. The taxane derivative of claim 4 wherein R$_1$ is phenyl or

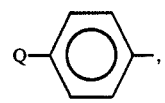

and Q is as defined in claim 1.

6. The taxane derivative of claim 1 wherein Z is —OH or —OCOCH$_3$.

7. The taxane derivative of claim 1 wherein R$_1$ or R$_3$ is phenyl and Z is —OH or —OCOCH$_3$.

8. The taxane derivative of claim 4 wherein R$_1$ is phenyl and Z is —OCOCH$_3$.

9. The taxane derivative of claim 3 wherein R$_3$ is phenyl and Z is —OCOCH$_3$.

10. The taxane derivative of claim 1 wherein R$_1$ or R$_3$ is phenyl, Z is —OCOCH$_3$, and the taxane has the 2'R, 3'S configuration.

11. A pharmaceutical composition which contains the taxane of claim 1 and one or more pharmacologically acceptable, inert or physiologically active diluents or adjuvants.

12. The composition of claim 11 wherein R$_1$ or R$_3$ is phenyl and Z is —OH or —OCOCH$_3$.

13. The composition of claim 11 wherein R$_1$ or R$_3$ is phenyl, Z is —OCOCH$_3$, and the taxane has the 2'R, 3'S configuration.

14. A taxane derivative having the formula:

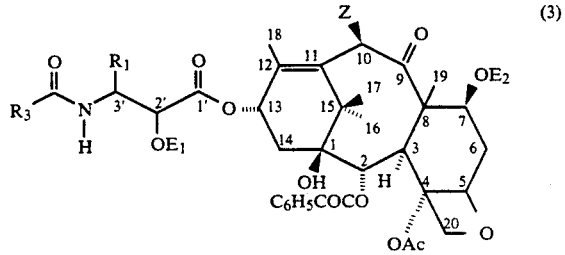

(3)

wherein
R₁ and R₃ are independently selected from the group consisting of phenyl, naphthyl, C₆H₅CHCH—,

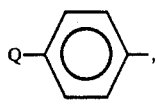

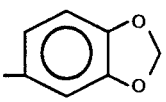

and

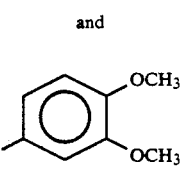

provided, however, R₁ and R₃ are not both phenyl;
Q is CH₃—, (CH₃)₃C—, CH₃O—, Cl, Br, F, or NO₂—, Z is —OT₁,
T₁ is hydrogen, hydroxyl protecting group, or —COT₂, T₂ is H, C₁-C₆ alkyl, C₂-C₆ alkenyl, C₂-C₆ alkynyl or monocylic aryl,
Ac is acetyl, and
E₁ and E₂ are independently selected from hydrogen and functional groups which increase the water solubility of the taxane derivative, the functional groups having the formula —COGCOR¹ wherein G is ethylene, propylene, —CH═CH—, 1,2-cyclohexane, or 1,2-phenylene,
R¹=OH base, NR²R³, OR³, SR³, OCH₂CONR⁴R⁵, or OH,
R²=hydrogen or methyl,
R³=(CH₂)ₙNR⁶R⁷ or (CH₂)ₙN⊕R⁶R⁷R⁸X⊖,
n=1 to 3,
R⁴=hydrogen, lower alkyl containing 1 to 4 carbons, or
R⁵=hydrogen, lower alkyl containing 1 to 4 carbons, benzyl, hydroxyethyl, CH₂CO₂H, dimethylaminoethyl, or
R⁶R⁷=lower alkyl containing 1 or 2 carbons, benzyl or R⁶ and
R⁷ together with the nitrogen atom of NR⁶R⁷ form the following rings

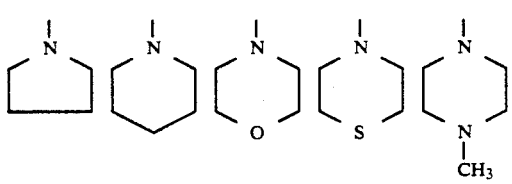

R⁸=lower alkyl containing 1 or 2 carbons or benzyl,
X⊖=halide, and
base=NH₃, (HOC₂H₄)₃N, N(CH₃)₃, CH₃N(C₂H₄OH)₂, NH₂(CH₂)₆NH₂, N-methylglucamine, NaOH, or KOH.
15. The taxane derivative of claim 14 wherein R₁ is

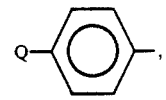

and Q is as defined in claim 25.
16. The taxane derivative of claim 14 wherein R₃ is

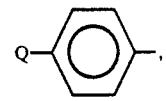

and Q is as defined in claim 25.
17. The taxane derivative of claim 14 wherein Z is —OH or —OCOCH₃.
18. A taxane derivative of the formula

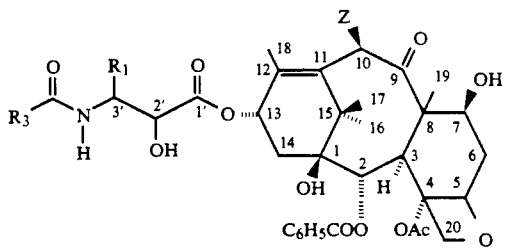

wherein
R₁ is selected from the group comprising phenyl, naphthyl, C₆H₅CHCH—, and

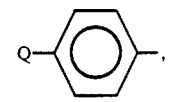

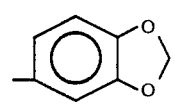

or

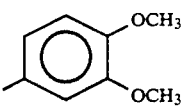

R₃ is selected from the group comprising naphthyl, C₆H₅CHCH—, and

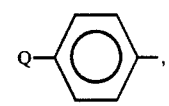

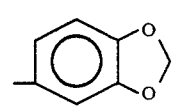

or

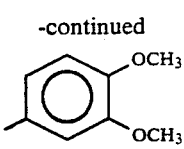

Q is $CH_3-$, $(CH_3)_3C-$, $CH_3-$, Cl, Br, F, or $NO_2$,
Z is $-OT_1$,
$T_1$ is hydrogen, hydroxyl protecting group, or $-COT_2$,
$T_2$ is H, $C_1$-$C_6$ alkyl, $C_2$-$C_6$ alkenyl, $C_2$-$C_6$ alkynyl or monocylic aryl, and
Ac is acetyl.

19. A taxane derivative of the formula

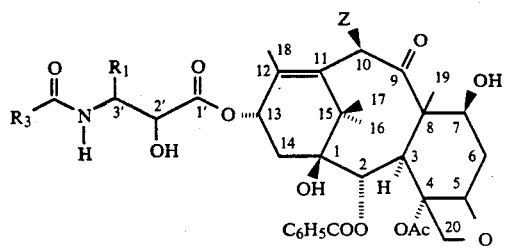

wherein
$R_1$ is selected from the group comprising phenyl, naphthyl, $C_6H_5CHCH-$, and

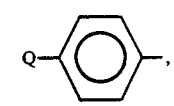

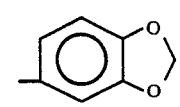

or

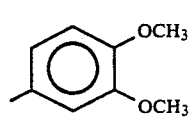

$R_3$ is selected from the group comprising phenyl, naphthyl, $C_6H_5CHCH-$, and

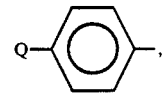

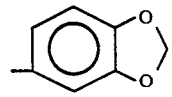

or

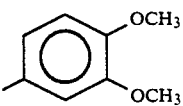

provided, however, $R_1$ and $R_3$ are not both phenyl,
Q is $CH_3-$, $(CH_3)_3C-$, $CH_3O-$, Cl, Br, F, or $NO_2$,
Z is $-OT_1$,
$T_1$ is hydrogen, hydroxyl protecting group, or $-COT_2$,
$T_2$ is H, $C_1$-$C_6$ alkyl, $C_2$-$C_6$ alkenyl, $C_2$-$C_6$ alkynyl or monocyclic aryl, and
Ac is acetyl.

20. A taxane derivative of the formula

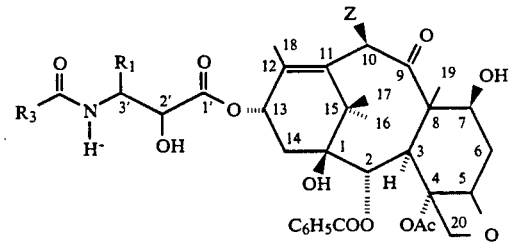

wherein
$R_1$ is selected from the group comprising phenyl, naphthyl, $C_6H_5CHCH-$, and

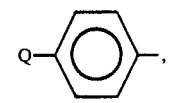

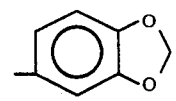

or

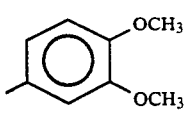

$R_3$ is selected from the group comprising phenyl, naphthyl, $C_6H_5CHCH-$, and

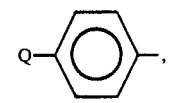

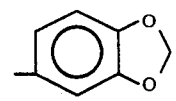

or

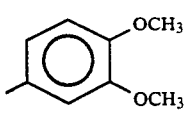

Q is $CH_3-$, $(CH_3)_3C-$, $CH_3O-$, Cl, Br, F, or $NO_2$,
Z is $-OCOT_2$,
$T_2$ is $C_2$-$C_6$ alkyl, $C_2$-$C_6$ alkenyl, $C_2$-$C_6$ alkynyl or monocyclic aryl, and
Ac is acetyl.

* * * * *

UNITED STATES PATENT AND TRADEMARK OFFICE
CERTIFICATE OF CORRECTION

PATENT NO. : 5,250,683
DATED : October 5, 1993
INVENTOR(S) : Robert A. Holton, et al.

It is certified that error appears in the above-identified patent and that said Letters Patent is hereby corrected as shown below:

Column 41, claim 1, line 60 "$(CH_3)_3C-,Cl$" should read ---$(CH_3)_3C-,CH_3O-,Cl$---.

Column 45, claim 18, line 8, "$CH_3-$" should read ---$CH_3O$---.

Signed and Sealed this

Thirty-first Day of May, 1994

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,250,683　　　　　　　　　　　　　　　Page 1 of 35

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

On the title page,
In the Abstract, formula (3) should read

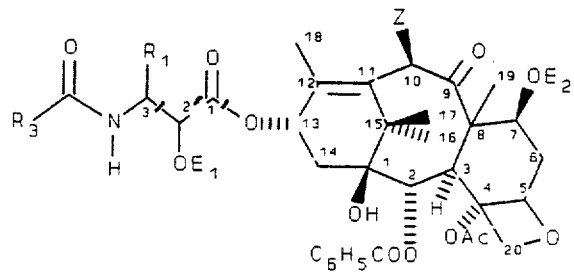

Please replace page 2, with the following:

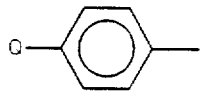

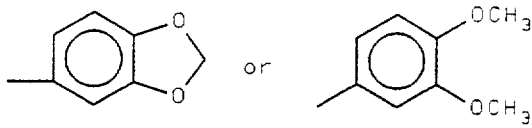

provided, however, $R_1$ and $R_3$ are not both phenyl;
　　Q is $CH_3-$, $(CH_3)_3C-$, $CH_3O-$, Cl, Br, F, $NO_2$,
　　Z is $-OT_1$,
　　$T_1$ is hydrogen, hydroxyl protecting group, or $-COT_2$,
　　$T_2$ is H, $C_1-C_6$ alkyl, $C_2-C_6$ alkenyl, $C_2-C_6$ alkynyl or monocylic aryl,
　　Ac is acetyl, and

UNITED STATES PATENT AND TRADEMARK OFFICE
CERTIFICATE OF CORRECTION

PATENT NO. : 5,250,683
DATED : October 5, 1993
INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

$E_1$ and $E_2$ are independently selected from hydrogen and functional groups which increase the water solubility of the taxane derivative are useful as antitumor agents. --.

In column 1, lines 25-35, formula (1) should read

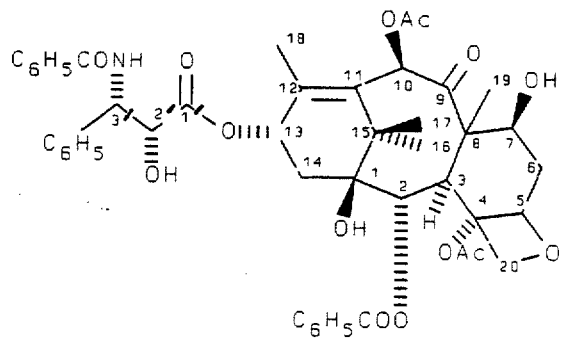

In column 1, line 59, "butoxy-carbonylamino" should read --butoxycarbonylamino--.

In column 2, lines 45-55 should be deleted.

In column 4, line 11 "diastereo-selective," should read --diastereoselective--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 4, lines 20-29, formula (5) should read

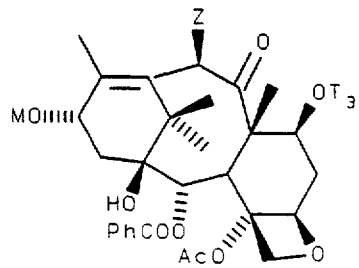

In column 4, line 33 "$C_1$-$C_6$ alkyl, $C_1$-$C_6$" should read --$C_1$-$C_6$ alkyl, $C_2$-$C_6$--.

In column 4, line 34 "$C_1$-$C_6$ alkynyl" should read -- $C_1C_2$ alkynyl --.

In column 4, lines 55-65, should read

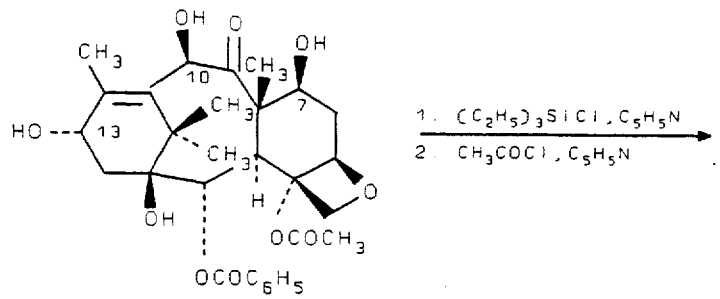

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 5, lines 1-10 should read

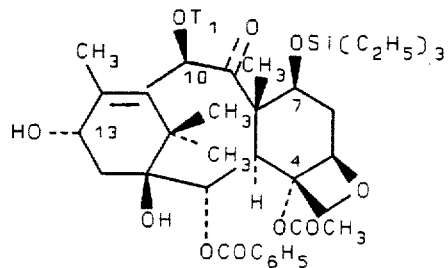

In column 6, lines 1-11, formula 10 should read

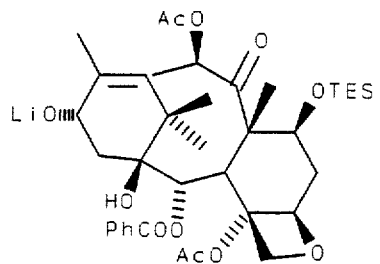

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 6, lines 20-30, the formula should read

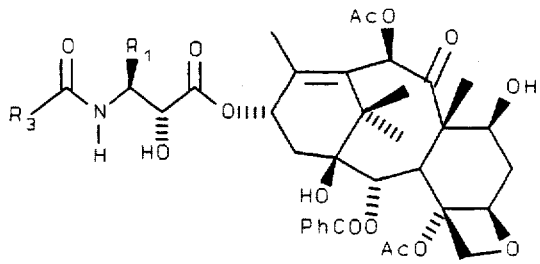

In column 7, line 7, "CH=CH" should read -- -CH=CH- --.

In column 7, line 12, "; (CH)$_n$" should read --; (CH$_2$)$_n$--.

In column 7, lines 40-50, the formula should read

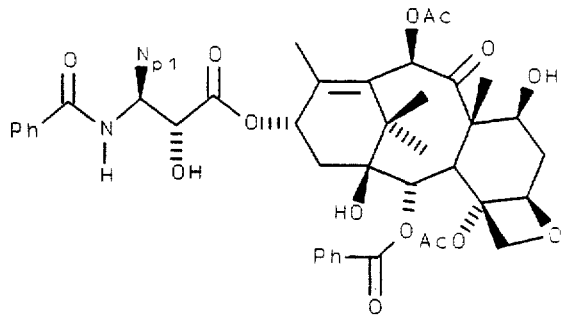

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 8, lines 38-46, the formula should read

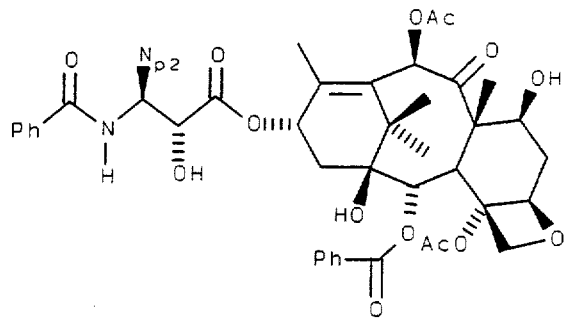

In column 8, line 68 "residuo" should read --residue--.

In column 9, line 18 "benzoate" should read --2H, benzoate--.

In column 9, line 24, "1H, H2$\delta$" should read --1H, H2$\beta$--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 9, lines 35-45 the formula should read

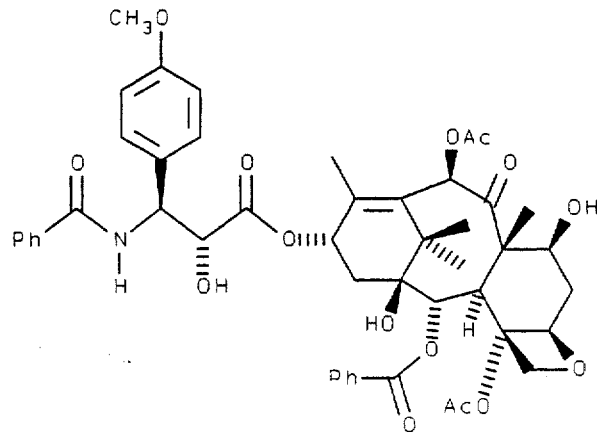

In column 9, line 63 "-3-desphenyl-" should read -- -3'-desphenyl- --.

In column 10, line 20 "ArOMe)," should read --Ar_OMe_),--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 10, lines 30-40 the formula should read

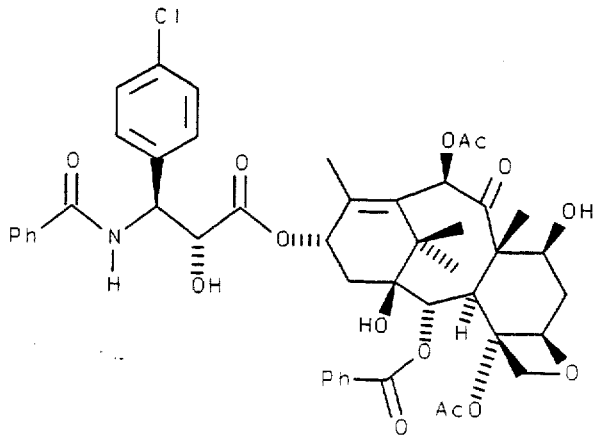

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 11, lines 20-30 the formula should read

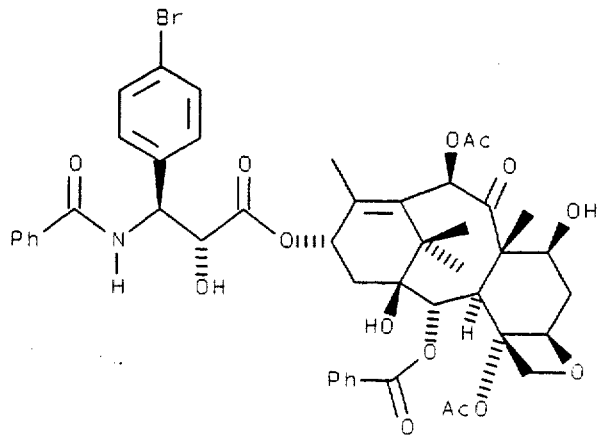

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 12, lines 13-24 the formula should read

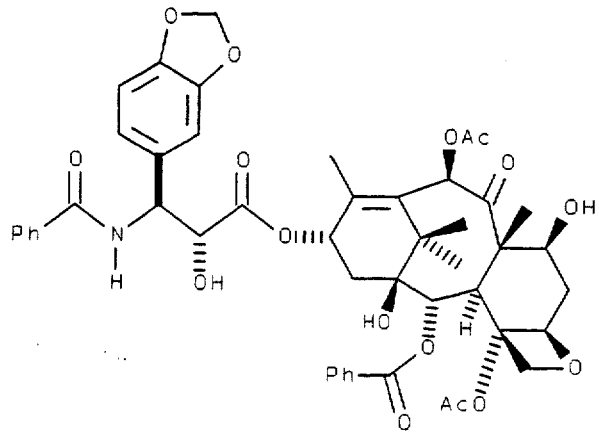

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh,
Seokchan Kim, and Ronald J. Beidiger It is certified that error appears in the above-identified patent and that said Letters Patent is hereby corrected as shown below:

In column 13, lines 10-20 the formula should read

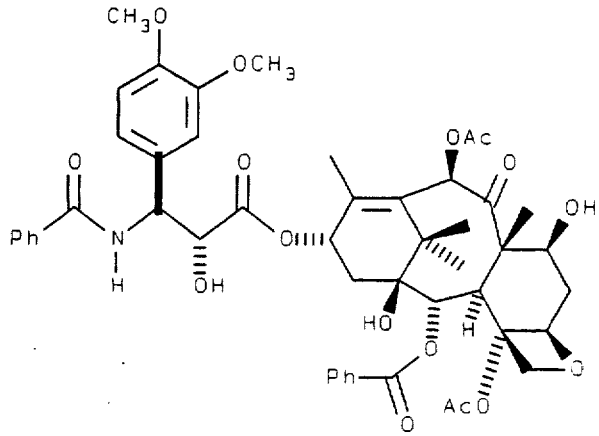

In column 13, line 63 "ArOMe" both instances, should read --Ar<u>O</u>Me--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 14, lines 5-15 the formula should read

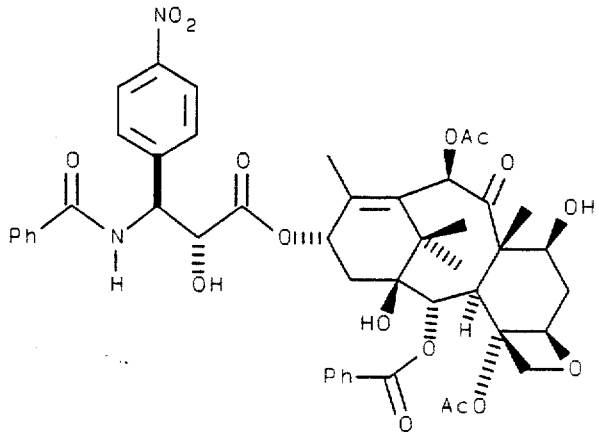

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 15, lines 5-15 the formula should read

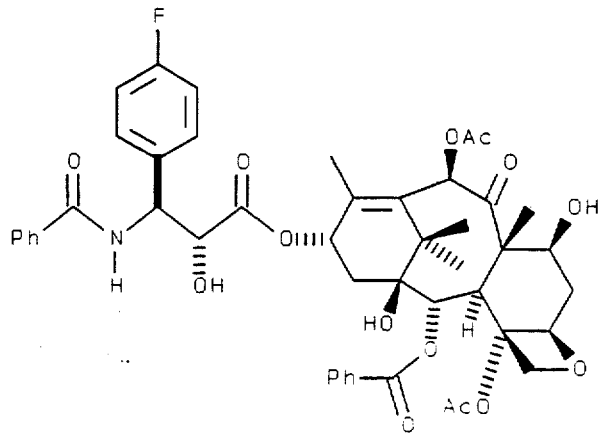

In column 16, lines 5-15 the formula should read

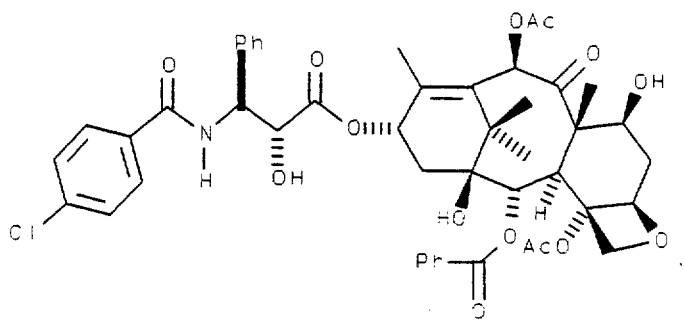

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 17, lines 20-30 the formula should read

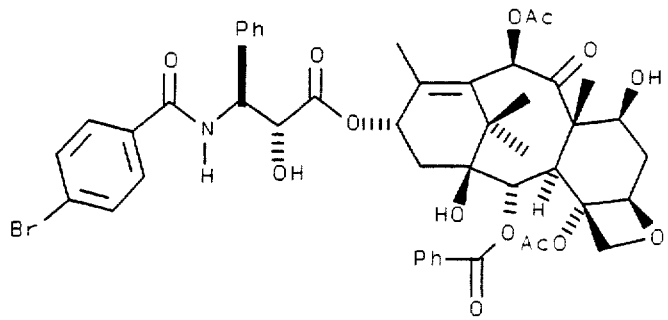

In column 18, lines 10-20 the formula should read

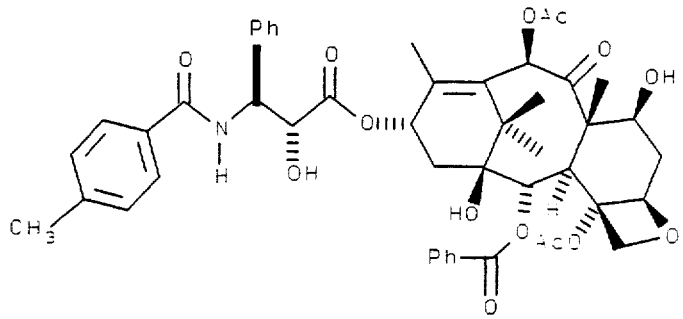

In column 18, line 63 "ArMe" should read --Ar*Me*--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 19, lines 1-12 the formula should read

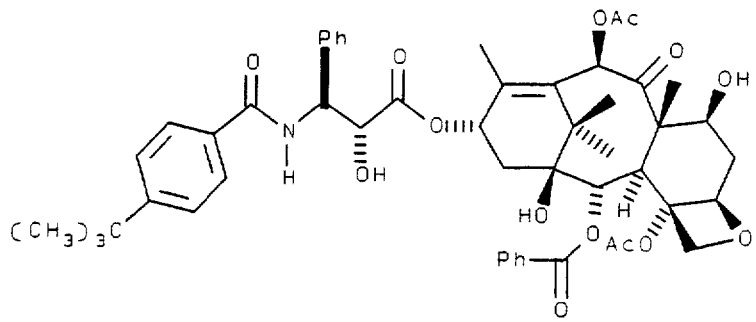

In column 19, line 54, "Ar$^t$Bu" should read --Ar$^t$<u>Bu</u>--.

In column 19, lines 58-68 the formula should read

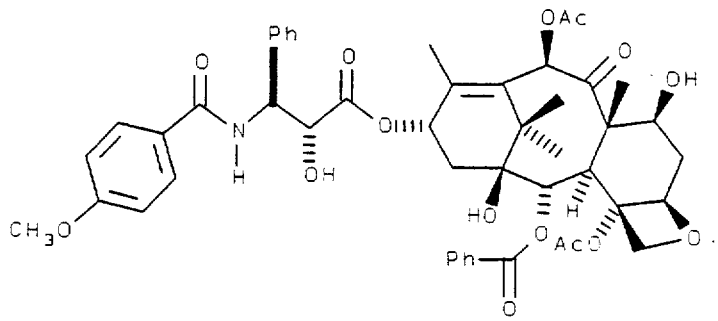

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 21, lines 5-15 the formula should read

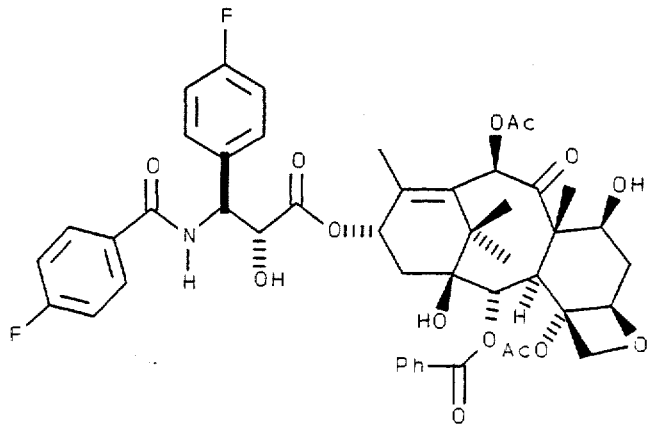

In column 21, line 22 "THE" should read --THF--.

In column 21, line 67, "2.3 (s," should read --2.36 (s,--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 22, lines 6-16 the formula should read

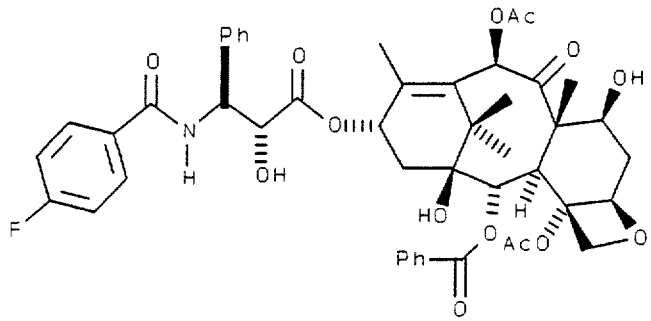

In column 22, line 19 "(4-fluoroobenzoyl)" should read --(4-fluorobenzoyl)--.

In column 22, line 36 "N-benzoyl" should read --N-debenzoyl--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 23, lines 5-15 the formula should read

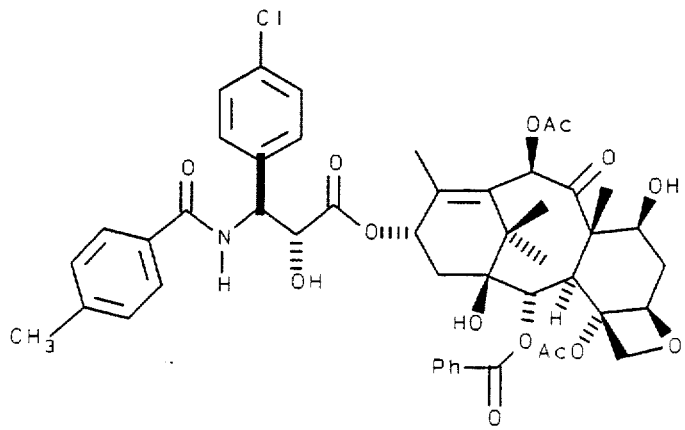

In column 23, line 65 "ArMe" should read --Ar<u>Me</u>--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 24, lines 20-30 the formula should read

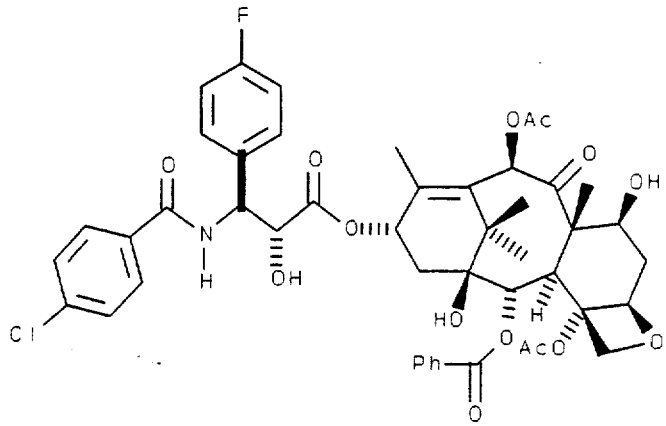

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 25, lines 15-25 the formula should read

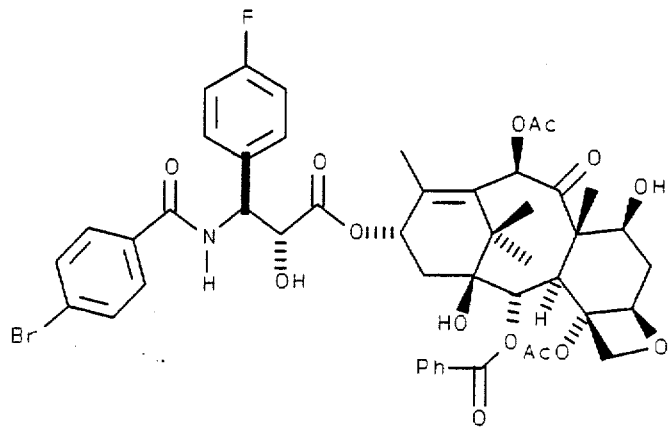

UNITED STATES PATENT AND TRADEMARK OFFICE
CERTIFICATE OF CORRECTION

PATENT NO. : 5,250,683
DATED : October 5, 1993
INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 26, lines 10-20 the formula should read

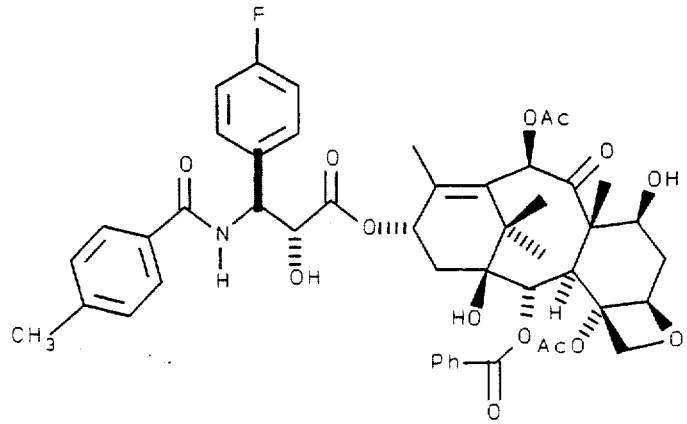

In column 27, line 1, "ArMe" should read --Ar_Me_--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 27, lines 8-20 the formula should read

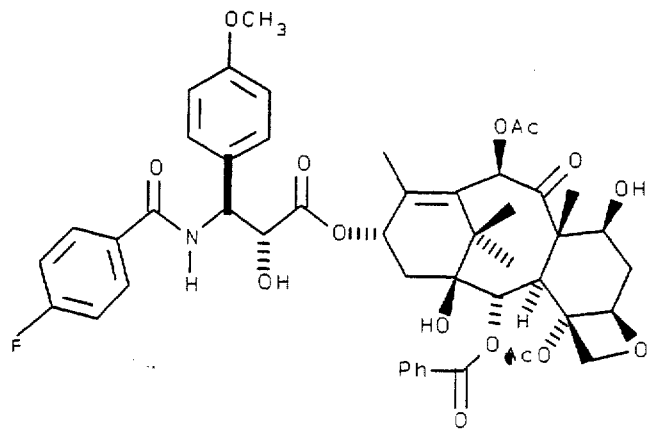

In column 27, line 64 "ArOMe" should read --Ar<u>OMe</u>--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 28, lines 5-15 the formula should read

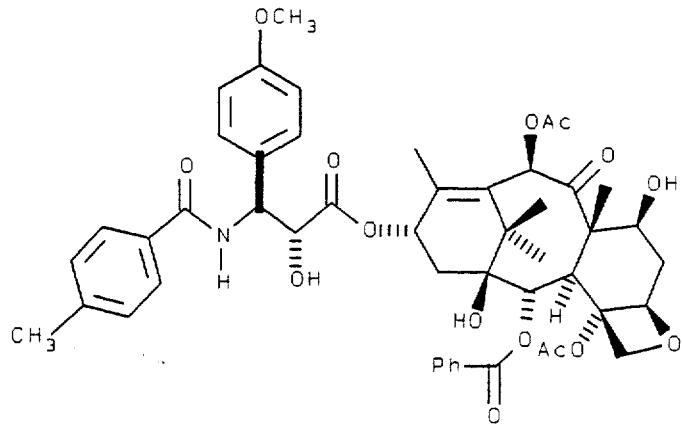

In column 28, line 63 "ArOMe" should read --Ar<u>OMe</u>--.

In column 28, line 65 "ArMe" should read --Ar<u>Me</u>--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 29, lines 5-15 the formula should read

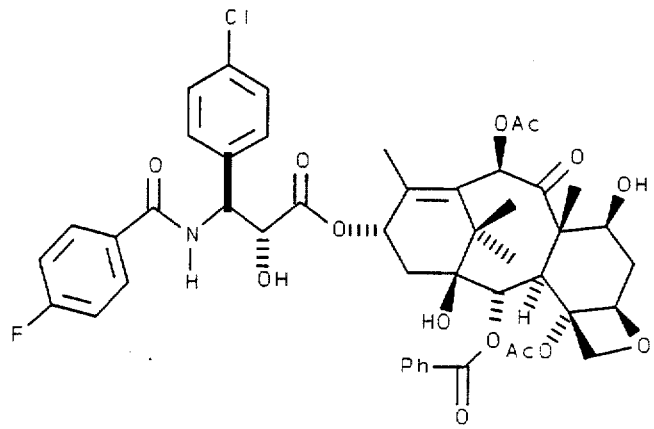

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 30, lines 5-15 the formula should read

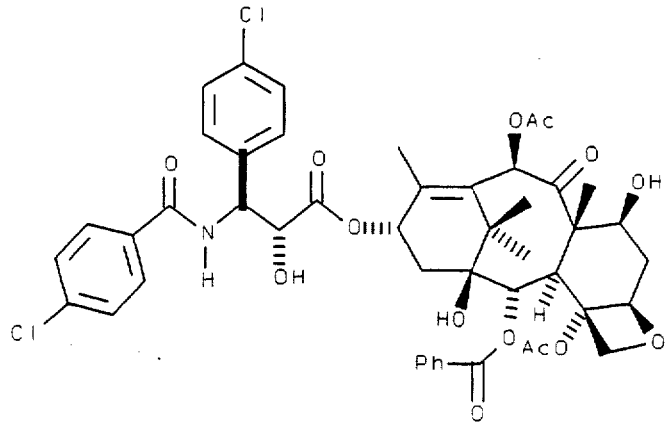

In column 30, line 37 "4-chloroobenzoyl" should read --4-chlorobenzoyl--.

In column 30, line 62, "14.8" should read --14.8,--.

In column 30, line 66, "14.8" should read --14.8,--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 31, lines 20-30 the formula should read

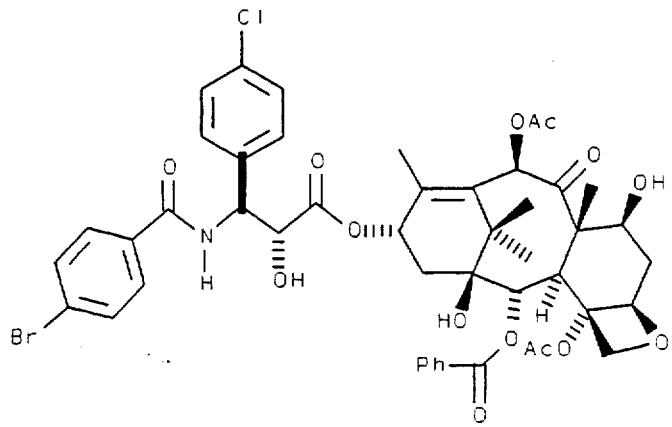

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 32, lines 15-25 the formula should read

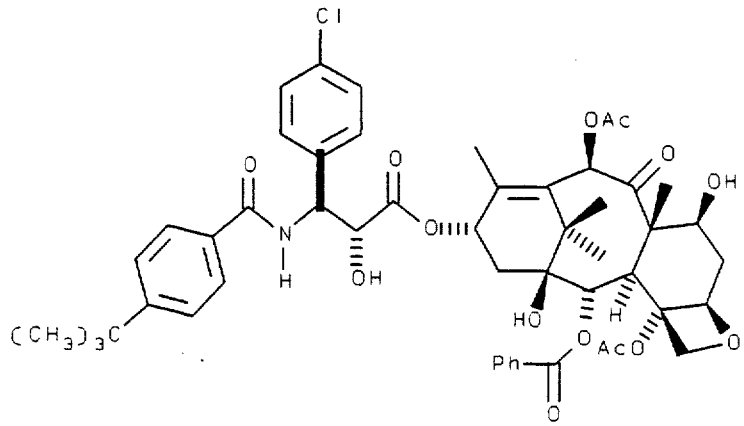

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 33, lines 10-20 the formula should read

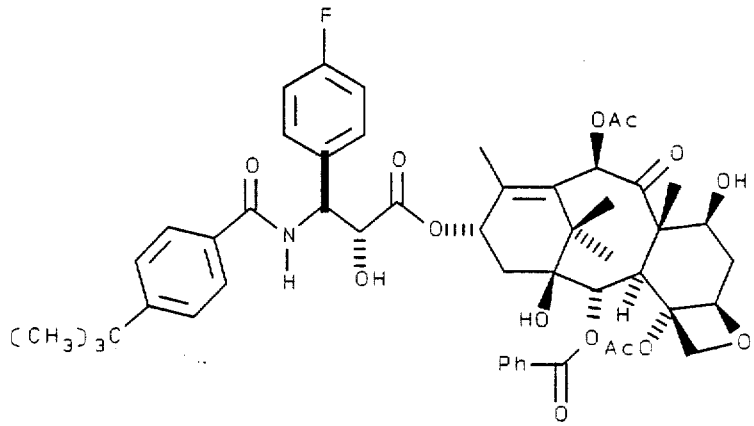

In column 34, line 33, "Ar$^t$Bu" should read --Ar$^t$<u>Bu</u>--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 34, lines 40-50 the formula should read

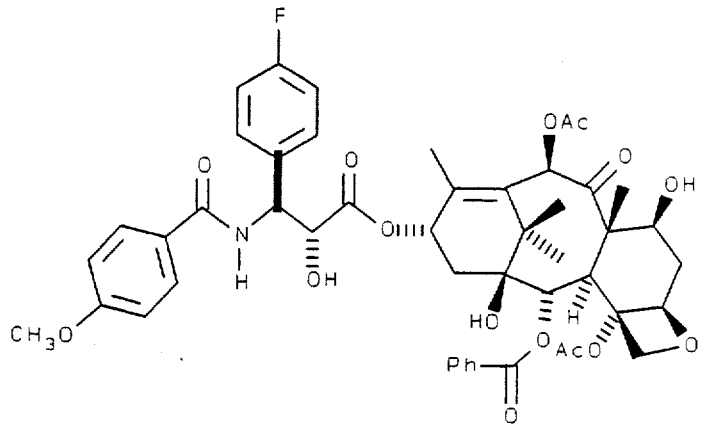

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 35, lines 34-45 the formula should read

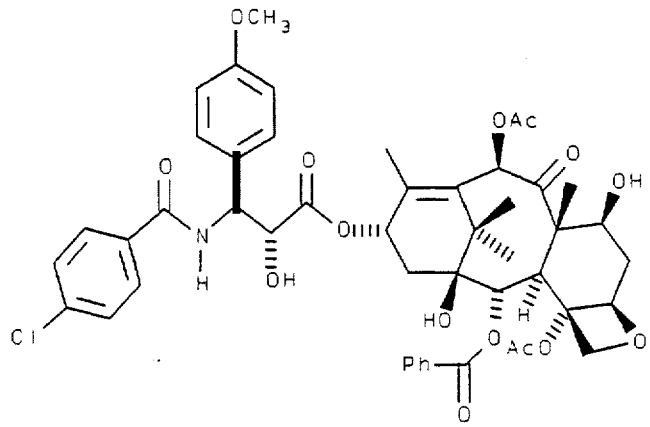

In column 36, line 22 "ArOMe" should read --Ar<u>O</u>Me--.

UNITED STATES PATENT AND TRADEMARK OFFICE
CERTIFICATE OF CORRECTION

PATENT NO. : 5,250,683
DATED : October 5, 1993
INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 36, lines 32-42 the formula should read

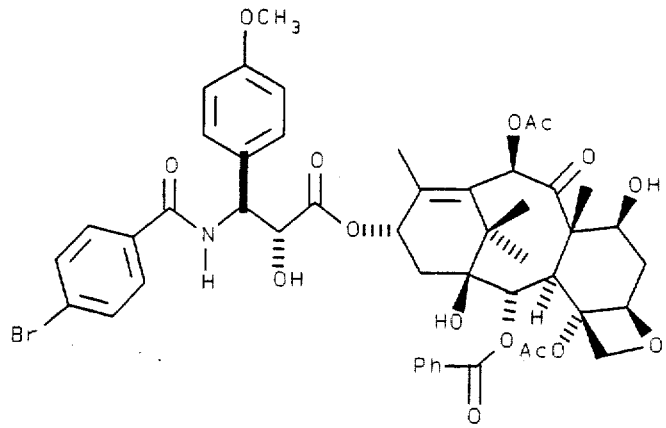

In column 36, line 62 "3'-(4-methox-" should read -- 3'-desphenyl-3'-(4-methox- --.

In column 37, line 18, "ArOMe" should read --Ar<u>O</u>Me--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 37, lines 28-38 the formula should read

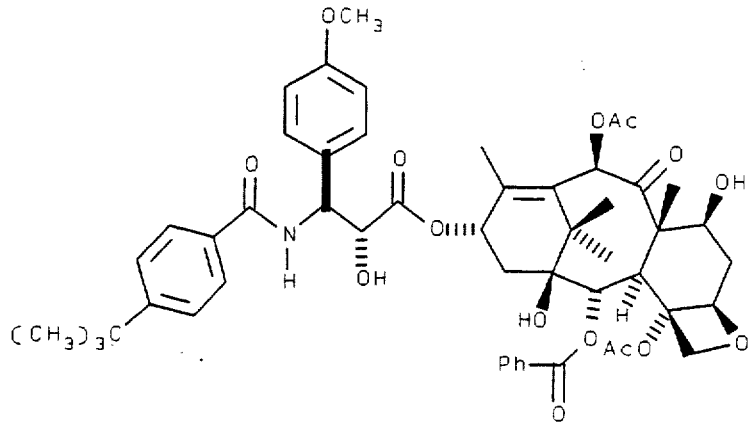

In column 38, line 44 "ArOMe" should read --Ar<u>OMe</u>--.

In column 38, line 49 "Ar$^t$Bu" should read --Ar$^t$<u>Bu</u>--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 38, line 55-65 the formula should read

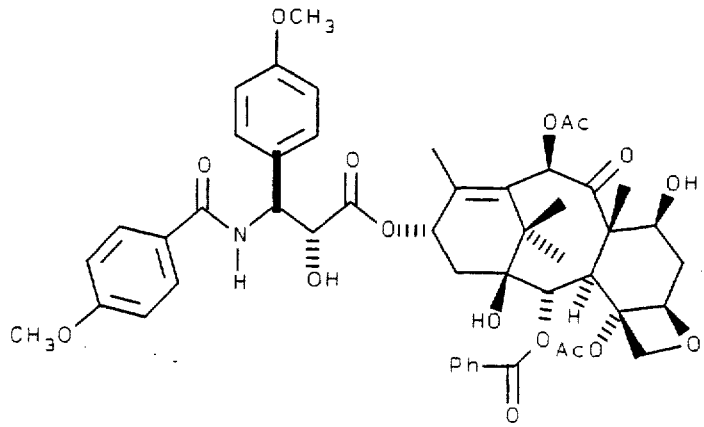

In column 39, line 4 "mmol))" should read --mmol)--.

In column 39, line 38, "H13);" should read --H13),--.

In column 39, lines 43 and 44 "ArOMe" should read --Ar<u>O</u>Me--.

In column 40, line 41 "line" should read --lines--.

In column 42, claim 9, line 42 "claim 3" should read --claim 2--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 42, claim 14, lines 58-68, formula (3) should read

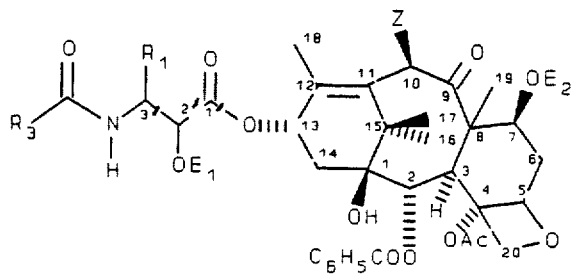

In column 43, claim 14, line 25 "Z is $-OT_1$," should start a new paragraph.

In column 43, line 27 "$T_2$ is H," should start a new paragraph.

In column 44, claim 15, line 8 "claim 25" should read --claim 14--.

UNITED STATES PATENT AND TRADEMARK OFFICE
CERTIFICATE OF CORRECTION

PATENT NO. : 5,250,683

DATED : October 5, 1993

INVENTOR(S) : Robert A. Holton, Hossain Nadizadeh, Seokchan Kim, and Ronald J. Beidiger It is certified that error appears in the above-identified patent and that said Letters Patent is hereby corrected as shown below:

In column 44, claim 16, line 16 "claim 25" should read --claim 14--.

Signed and Sealed this

Ninth Day of June, 1998

Attest:

BRUCE LEHMAN

Attesting Officer

Commissioner of Patents and Trademarks